(12) United States Patent
Rockwell et al.

(10) Patent No.: US 6,811,779 B2
(45) Date of Patent: Nov. 2, 2004

(54) METHODS FOR REDUCING TUMOR GROWTH WITH VEGF RECEPTOR ANTIBODY COMBINED WITH RADIATION AND CHEMOTHERAPY

(75) Inventors: Patricia Rockwell, West Redding, CT (US); Neil I. Goldstein, Maplewood, NJ (US)

(73) Assignee: ImClone Systems Incorporated, New York, NY (US)

( * ) Notice: Subject to any disclaimer, the term of this patent is extended or adjusted under 35 U.S.C. 154(b) by 0 days.

(21) Appl. No.: 09/798,689

(22) Filed: Mar. 2, 2001

(65) Prior Publication Data

US 2003/0103973 A1 Jun. 5, 2003

Related U.S. Application Data

(63) Continuation-in-part of application No. 09/401,163, filed on Sep. 22, 1999, now Pat. No. 6,365,157, which is a continuation of application No. 08/967,113, filed on Nov. 10, 1997, now Pat. No. 6,448,077, which is a continuation-in-part of application No. 08/706,804, filed on Sep. 3, 1996, now Pat. No. 5,861,499, which is a continuation-in-part of application No. 08/476,533, filed on Jun. 7, 1995, now abandoned, which is a continuation of application No. 08/326,552, filed on Oct. 20, 1994, now Pat. No. 5,840,301, which is a continuation-in-part of application No. 08/196,041, filed on Feb. 10, 1994, now abandoned.

(51) Int. Cl.$^7$ .............................................. A61K 39/395
(52) U.S. Cl. ................ 424/135.1; 424/142.1; 424/143.1; 424/155.1; 424/174.1
(58) Field of Search ............................ 424/1.11, 135.1, 424/155.1, 142.1, 143.1, 174.1

(56) References Cited

U.S. PATENT DOCUMENTS

| | | | |
|---|---|---|---|
| 5,185,438 A | 2/1993 | Lemischka | |
| 5,270,458 A | 12/1993 | Lemischka | |
| 5,548,065 A | 8/1996 | Lemischka | |
| 5,621,090 A | 4/1997 | Lemischka | |
| 5,747,651 A | 5/1998 | Lemischka | |
| 5,851,999 A | 12/1998 | Ullrich et al. | |

FOREIGN PATENT DOCUMENTS

| | | |
|---|---|---|
| CA | 2085291 | 1/1994 |
| WO | WO 91/02058 | 2/1991 |
| WO | WO 92/14748 | 9/1992 |
| WO | WO 93/11238 | 6/1993 |
| WO | WO 93/12220 | 6/1993 |
| WO | WO 93/21319 | 10/1993 |
| WO | WO 94/10202 | 5/1994 |
| WO | WO 94/10331 | 5/1994 |
| WO | WO 94/11499 | 5/1994 |
| WO | WO 95/21868 | 8/1995 |

OTHER PUBLICATIONS

Kaipainen et al., J. Exp. Med. 178:2077–2088 (Dec. 1993).
Kim et al., Nature 362:841–844 (Apr. 29, 1993).
Matthews et al., Proc. Natl. Acad. Sci. USA, 88:9026–9030 (Oct. 1991).
Millauer et al., Cell 72:835–846 (Mar. 1993).
Plate et al., Cancer Res. 53:5822–5827 (Dec. 1, 1993).
Shibuya et al., Oncogene 5:519–524 (Apr. 1990).
Terman et al., Oncogene 6:1677–1683 (Sep. 1991).
Plate et al., Nature 359:845–848 (Oct. 1992).
Leung et al., Science 246:1306–1309 (Dec. 1989).
Kim, K.J. et al., Growth Factors 7:53–64 (1992).
Morrison, S.L. et al., Proc. Natl. Acad. Sci. USA 81:6851–6855 (Nov. 1984).
Co., M.S. et al., Nature 351:501–502 (Jun. 1991).
Folkman, J. et al., Science 235:442–447 (Jan 23, 1987).
Rockwell et al., Molecular and Cellular Differentiation 3:91–109 (1995).
Rockwell et al., Molecular and Cellular Differentiation 3:315–335 (1995).

*Primary Examiner*—Jeffrey Stucker
(74) *Attorney, Agent, or Firm*—Kenyon & Kenyon

(57) ABSTRACT

The invention provides a method of reducing tumor growth in a mammal comprising treating the mammal with an effective amount of a combination of a VEGF receptor antagonist and radiation. In addition, the invention provides a method of reducing tumor growth in a mammal comprising treating the mammal with an effective amount of a combination of a VEGF receptor antagonist and a chemotherapeutic agent.

27 Claims, 24 Drawing Sheets

Western Blot of Flk-1/SEAPS Immunoprecipitation with MAb DC101

Inhibition of VEGF-Flk-1/fms activation by prebound MAb DC101

Assay conditions:
MAb (5µg/ml):  — + — —  P(+) C(+)
VEGF (ng/ml):  — — 20 40 40 40

−200

Probe: Anti-Ptyr

Assay conditions:  P: MAb prebound 15'; VEGF 15'
C: Competitive assay; MAb + VEGF 15'

Immunoprecipitation of phosphorylated flk-1/fms from VEGF stimulated flk-1/fms transfected 3T3 cells.

Anti-pTyr

Antibodies:  1) Rat anti-flk-2 $IgG_{2a}$ 2A13
2) Rat anti-flk-1 $IgG_1$ DC101
3) Rat anti-flk-2 $IgG_1$ 23H7
4) Rabbit anti-fms polyclonal IM 133

Treatment of Glioblastoma Xenografs with Rat anti-flk-2 MAb

Treatment of Glioblastoma Xenografs with Rat anti-Flk-1 MAb

Statistical Analysis:

Flk-1 slope = 16.09
Flk-2 slope = 37.39
p value for Flk-1 versus Flk-2 tumor size = 0.0001

```
HindIII
GAACTTATGGGATGGTCATGTATCATCCTTTTTCTAGTAGCAACTGCAACTGGAGTACAT
      M   G   W   S   C   I   I   L   F   L   V   A   T   A   T   G   V   H
          → leader TCACAGGTCAAGCTGCAGCAGTCTGGGGCAGAGCTTGTGGGGTCAGGGGCCTCAGTCAAA
  S   Q   V   K   L   Q   Q   S   G   A   E   L   V   G   S   G   A   S   V   K
      → VH TTGTCCTGCACAACTTCTGGCTTCAACATTAAAGACTTCTATATGCACTGGGTGAAGCAG
  L   S   C   T   T   S   G   F   N   I   K   D   F   Y   M   H   W   V   K   G
                          ─────────────────────────────
                                    CDR-H1

AGGCCTGAACAGGGCCTGGAGTGGATTGGATGGATTGATCCTGAGAATGGTGATTCTGAT
  R   P   E   Q   G   L   E   W   I   G   W   I   D   P   E   N   G   D   S   D
                                      ───────────────────────────────
                                                   CDR-H2

TATGCCCCGAAGTTCCAGGGCAAGGCCACCATGACTGCAGACTCATCCTCCAACACAGCC
  Y   A   P   K   F   Q   G   K   A   T   M   T   A   D   M   S   S   N   T   A
  ─────────────────────

TACCTGCAGCTCAGCAGCCTGACATCTGAGGACACTGCCGTCTATTACTGTAATGCATAC
  Y   L   Q   L   S   S   L   T   S   E   D   T   A   V   Y   Y   C   N   A   Y
                                                                          ─

TATGGTGACTACGAAGGCTACTGGGGCCAAGGGACCACGGTCACCGTCTCCTCAGGTGAG
  Y   G   D   Y   E   G   Y   W   G   Q   G   T   T   V   T   V   S   S
  ─────────────────────
       CDR-H3

BamHI
TGGATCC

HindIII
AGGCTTATGGGATGGTCATGTATCATCCTTTTTCTAGTAGCAACTGCAACTGGAGTACAT
      M   G   W   S   C   I   I   L   F   L   V   A   T   A   T   G   V   H
          → leader TCAGACATCGAGCTCACTCAGTCTCCAGCAATCATGTCTGCATCTCCAGGGGAGAAGGTC
  S   D   I   E   L   T   Q   S   P   A   I   M   S   A   S   P   G   E   K   V
      → VL ACCATAACCTGCAGTGCCAGCTCAAGTGTAAGTTACATGCACTGGTTCCAGCAGAAGCCA
  T   I   T   C   S   A   S   S   S   V   S   Y   M   H   W   F   Q   Q   K   P
                  ───────────────────────────────
                              CDR-L1

GGSACTTCTCCCAAACTCTGGATTTATAGCACATCCAACCTGGCTTCTGGAGTCCCTGCT
  G   T   S   P   K   L   W   I   Y   S   T   S   N   L   A   S   V   P   A
                                      ───────────────────────
                                              CDR-L2

CGCTTCAGTGGCAGTGGATCTGGGACCTCTTACTCTCTCACAATCAGCCGAATGGAGGCT
  R   F   S   G   S   G   S   G   T   S   Y   S   L   T   I   S   R   M   E   A

GAAGATGCTGCCACTTATTACTGCCAGCAAAGGAGTAGTTACCCATTCACGTTCGGCTCG
  E   D   A   A   T   Y   Y   C   Q   Q   R   S   S   Y   P   F   T   F   G   S
                                      ───────────────────────────────
                                                    CDR-L3
                                BamHI
GGGACCAAGCTGGAAATAAAACGTGAGTGGATCC
  G   T   K   L   E   I   K
```

Figure 19

METHODS FOR REDUCING TUMOR GROWTH WITH VEGF RECEPTOR ANTIBODY COMBINED WITH RADIATION AND CHEMOTHERAPY

This application is a continuation-in-part of Ser. No. 09/401,163, filed on Sep. 22, 1999, now U.S. Pat. No. 6,365,157; which is a continuation of Ser. No. 08/967,113 filed on Nov. 10, 1997, now U.S. Pat. No. 6,448,077; which is a continuation-in-part of U.S. Pat. No. 5,861,499 Ser. No. 08/706/804 now which is a continuation-in-part of Ser. No. 08/476,533 filed Jun. 7, 1995, abandoned; which is a continuation of Ser. No. 08/326,552 U.S. Pat. No. 5,840,301 filed Oct. 20, 1994; which is a continuation-in-part of Ser. No. 08/196,041 filed now abandoned. The entire disclosure of the aforementioned prior applications are incorporated herein by reference.

BACKGROUND OF THE INVENTION

Angiogenesis is the process of developing new blood vessels that involves the proliferation, migration and tissue infiltration of capillary endothelial cells from pre-existing blood vessels. Angiogenesis is important in normal physiological processes including embryonic development, follicular growth, and wound healing as well as in pathological conditions involving tumor growth and non-neoplastic diseases involving abnormal neovascularization, including neovascular glaucoma (Folkman, J. and Klagsbrun, M. Science 235:442–447 (1987)).

The vascular endothelium is usually quiescent and its activation is tightly regulated during angiogenesis. Several factors have been implicated as possible regulators of angiogenesis in vivo. These include transforming growth factor (TGFb), acidic and basic fibroblast growth factor (aFGF and bFGF), platelet derived growth factor (PDGF), and vascular endothelial growth factor (VEGF) (Klagsbrun, M. and D'Amore, P. (1991) Annual Rev. Physiol. 53: 217–239). VEGF, an endothelial cell-specific mitogen, is distinct among these factors in that it acts as an angiogenesis inducer by specifically promoting the proliferation of endothelial cells.

VEGF is a homodimeric glycoprotein consisting of two 23 kD subunits with structural similarity to PDGF. Four different monomeric isoforms of VEGF exist resulting from alternative splicing of mRNA. These include two membrane bound forms ($VEGF_{206}$ and $VEGF_{189}$) and two soluble forms ($VEGF_{165}$ and $VEGF_{121}$). In all human tissues except placenta, $VEGF_{165}$ is the most abundant isoform.

VEGF is expressed in embryonic tissues (Breier et al., Development (Camb.) 114:521 (1992)), macrophages, proliferating epidermal keratinocytes during wound healing (Brown et al., J. Exp. Med., 176:1375 (1992)), and may be responsible for tissue edema associated with inflammation (Ferrara et al., Endocr. Rev. 13:18 (1992)). In situ hybridization studies have demonstrated high VEGF expression in a number of human tumor lines including glioblastoma multiforme, hemangioblastoma, central nervous system neoplasms and AIDS-associated Kaposi's sarcoma (Plate, K. et al. (1992) Nature 359: 845–848; Plate, K. et al. (1993) Cancer Res. 53: 5822–5827; Berkman, R. et al. (1993) J. Clin. Invest. 91: 153–159; Nakamura, S. et al. (1992) AIDS Weekly, 13 (1)). High levels of VEGF were also observed in hypoxia induced angiogenesis (Shweiki, D. et al. (1992) Nature 359: 843–845).

The biological response of VEGF is mediated through its high affinity VEGF receptors which are selectively expressed on endothelial cells during embryogenesis (Millauer, B., et al. (1993) Cell 72: 835–846) and during tumor formation. VEGF receptors typically are class III receptor-type tyrosine kinases characterized by having several, typically 5 or 7, immunoglobulin-like loops in their amino-terminal extracellular receptor ligand-binding domains (Kaipainen et al., J. Exp. Med. 178:2077–2088 (1993)). The other two regions include a transmembrane region and a carboxy-terminal intracellular catalytic domain interrupted by an insertion of hydrophilic interkinase sequences of variable lengths, called the kinase insert domain (Terman et al., Oncogene 6:1677–1683 (1991). VEGF receptors include FLT-1, sequenced by Shibuya M. et al., Oncogene 5, 519–524 (1990); KDR, described in PCT/US92/01300, filed Feb. 20, 1992, and in Terman et al., Oncogene 6:1677–1683 (1991); and FLK-1, sequenced by Matthews W. et al. Proc. Natl. Acad. Sci. USA, 88:9026–9030 (1991).

High levels of FLK-1 are expressed by endothelial cells that infiltrate gliomas (Plate, K. et al., (1992) Nature 359: 845–848). FLK-1 levels are specifically upregulated by VEGF produced by human glioblastomas (Plate, K. et al. (1993) Cancer Res. 53: 5822–5827). The finding of high levels of FLK-1 expression in glioblastoma associated endothelial cells (GAEC) indicates that receptor activity is probably induced during tumor formation since FLK-1 transcripts are barely detectable in normal brain endothelial cells. This upregulation is confined to the vascular endothelial cells in close proximity to the tumor. Blocking VEGF activity with neutralizing anti-VEGF monoclonal antibodies (mAbs) resulted in an inhibition of the growth of human tumor xenografts in nude mice (Kim, K. et al. (1993) Nature 362: 841–844), indicating a direct role for VEGF in tumor-related angiogenesis.

Although the VEGF ligand is upregulated in tumor cells, and its receptors are upregulated in tumor infiltrated vascular endothelial cells, the expression of the VEGF ligand and its receptors is low in normal cells that are not associated with angiogenesis. Therefore, such normal cells would not be affected by blocking the interaction between VEGF and its receptors to inhibit angiogenesis, and therefore tumor growth.

One advantage of blocking the VEGF receptor as opposed to blocking the VEGF ligand to inhibit angiogenesis, and thereby to inhibit pathological conditions such as tumor growth, is that fewer antibodies may be needed to achieve such inhibition. Furthermore, receptor expression levels may be more constant than those of the environmentally induced ligand. Another advantage of blocking the VEGF receptor is that more efficient inhibition may be achieved when combined with blocking of the VEGF ligand.

An object of the present invention is to provide VEGF antagonists, e.g. antibodies, which neutralize the interaction between VEGF and its receptor by binding to a VEGF receptor and thereby preventing VEGF phosphorylation of the receptor. A further object of this invention is to provide methods to inhibit angiogenesis and thereby to reduce tumor growth in mammals using such VEGF antagonists, and in particular using such VEGF antagonists combined with radiation and chemotherapy.

SUMMARY OF THE INVENTION

The present invention provides a method of reducing tumor growth in a mammal comprising treating the mammal with an effective amount of a combination of a VEGF receptor antagonist and radiation. In addition, the invention provides a method of reducing tumor growth in a mammal comprising treating the mammal with an effective amount of a combination of a VEGF receptor antagonist and a chemotherapeutic agent. In addition, the invention provides a method of reducing tumor growth in a mammal comprising treating the mammal with an effective amount of a combination of a VEGF receptor antagonist, radiation and a chemotherapeutic agent.

DESCRIPTION OF THE FIGURES

FIG. 2a: Competitive inhibition assay indicating the effect of anti-FLK-1 monoclonal antibody DC-101 on $VEGF_{165}$ induced phosphorylation of the FLK-1/fms receptor in transfected 3T3 cells. FIG. 2b: Sensitivity of VEGF induced phosphorylation of the FLK-1/fms receptor to inhibition by monoclonal antibody DC-101. C441 cells were assayed at maximal stimulatory concentrations of $VEGF_{165}$ (40 ng/ml) combined with varying levels of the antibody.

FIG. 3a: Titration of VEGF-induced phosphorylation of the FLK-1/fms receptor in the presence of mAb DC-101. C441 cells were stimulated with the concentrations of VEGF indicated in the presence (Lanes 1 to 4) or absence (Lanes 5 to 8) of 5 µg/ml of MAb DC-101. Unstimulated cells assayed in the presence of antibody (Lane 9) serves as the control. FIG. 3b: Densitometry scans of the level of phosphorylated receptor in each lane in FIG. 3a relative to each VEGF concentration is plotted to show the extent of Mab inhibition at excess ligand concentrations. Cell lysates were prepared for detection by anti-phosphotyrosine as described in the Examples below.

FIG. 14b: Reduction in tumor growth in individual animals with the control 2A13 group (rat anti-flk-2 monoclonal antibody).

FIG. 19: The nucleotide and deduced amino acid sequence of $V_H$ and $V_L$ chains of c-p1C11.

DETAILED DESCRIPTION OF THE INVENTION

Figure 1:
FIG. 1: Western Blot of FLK-1/SEAPS immunoprecipitation with monoclonal antibody DC-101 demonstrating that DC-101 immunoprecipitates murine FLK-1:SEAPS but not SEAPS alone.

The present invention provides methods of reducing tumor growth in mammals with radiation and/or chemotherapy in combination with VEGF receptor antagonists.

In a preferred embodiment, there is synergy when tumors, including human tumors, are treated with a VEGF receptor antagonist in conjunction with chemotherapeutic agents or radiation or combinations thereof. In other words, the inhibition of tumor growth by a VEGF receptor antagonist is enhanced more than expected when combined with chemotherapeutic agents or radiation or combinations thereof. Synergy may be shown, for example, by greater inhibition of tumor growth with combined treatment than would be expected from the additive effect of treatment with a VEGF receptor antagonist and a chemotherapeutic agent or radiation. Preferably, synergy is demonstrated by remission of the cancer where remission is not expected from treatment with a combination of a VEGF receptor antagonist and a chemotherapeutic agent or radiation. (See Example VIII.)

The VEGF receptor antagonist is administered before, during, or after commencing chemotherapy or radiation therapy, as well as any combination thereof, i.e. before and during, before and after, during and after, or before, during, and after commencing the chemotherapy and/or radiation therapy. For example when the VEGF receptor antagonist is an antibody, the antibody is typically administered between 1 and 30 days, preferably between 3 and 20 days, more preferably between 5 and 12 days before commencing radiation therapy and/or chemotherapy.

Radiation

The source of radiation, used in combination with a VEGF receptor antagonist, can be either external or internal to the patient being treated. When the source is external to the patient, the therapy is known as external beam radiation therapy (EBRT). When the source of radiation is internal to the patient, the treatment is called brachytherapy (BT).

The radiation is administered in accordance with well known standard techniques using standard equipment manufactured for this purpose, such as AECL Theratron and Varian Clinac. The dose of radiation depends on numerous factors as is well known in the art. Such factors include the organ being treated, the healthy organs in the path of the radiation that might inadvertently be adversely affected, the tolerance of the patient for radiation therapy, and the area of the body in need of treatment. The dose will typically be between 1 and 100 Gy, and more particularly between 2 and 80 Gy. Some doses that have been reported include 35 Gy to the spinal cord, 15 Gy to the kidneys, 20 Gy to the liver, and 65–80 Gy to the prostate. It should be emphasized, however, that the invention is not limited to any particular dose. The dose will be determined by the treating physician in accordance with the particular factors in a given situation, including the factors mentioned above.

The distance between the source of the external radiation and the point of entry into the patient may be any distance that represents an acceptable balance between killing target cells and minimizing side effects. Typically, the source of the external radiation is between 70 and 100 cm from the point of entry into the patient.

Brachytherapy is generally carried out by placing the source of radiation in the patient. Typically, the source of radiation is placed approximately 0–3 cm from the tissue being treated. Known techniques include interstitial, intercavitary, and surface brachytherapy. The radioactive seeds can be implanted permanently or temporarily. Some typical radioactive atoms that have been used in permanent implants include iodine-125 and radon. Some typical radioactive atoms that have been used in temporary implants include radium, cesium-137, and iridium-192. Some additional radioactive atoms that have been used in brachytherapy include americium-241 and gold-198.

The dose of radiation for brachytherapy can be the same as that mentioned above for external beam radiation therapy. In addition to the factors mentioned above for determining the dose of external beam radiation therapy, the nature of the radioactive atom used is also taken into account in determining the dose of brachytherapy.

Chemotherapy

Chemotherapeutic agents include all chemical compounds that are effective in inhibiting tumor growth.

The administration of chemotherapeutic agents can be accomplished in a variety of ways including systemically by the parenteral and enteral routes. In one embodiment, the VEGF receptor antagonist and the chemotherapeutic agent are administered as separate molecules. In another embodiment, the VEGF receptor antagonist is attached, such as, for example, by conjugation, to a chemotherapeutic agent.

Examples of chemotherapeutic agents include alkylating agents, for example, nitrogen mustards, ethyleneimine compounds and alkyl sulphonates; antimetabolites, for example, folic acid, purine or pyrimidine antagonists, mitotic inhibitors, for example, vinca alkaloids and derivatives of podophyllotoxin; cytotoxic antibiotics; compounds that damage or interfere with DNA expression; and growth factor receptor antagonists.

Additionally, chemotherapeutic agents include antibodies, biological molecules and small molecules, as described above.

Particular examples of chemotherapeutic agents or chemotherapy include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin, paclitaxel (taxol), docetaxel (taxotere), aldesleukin, asparaginase, busulfan, carboplatin, cladribine, dacarbazine, floxuridine, fludarabine, hydroxyurea, ifosfamide, interferon alpha, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil, taxol and combinations thereof.

Growth factor receptor antagonists (other than VEGFR antagonists) that can be used as chemotherapeutic agents include all substances that inhibit the stimulation of a growth factor receptor by a growth factor receptor ligand. Such inhibition of stimulation inhibits the growth of cells that express the growth factor receptor. Some examples of growth factor receptors involved in tumorigenesis are the receptors for epidermal growth factor (EGFR), platelet-derived growth factor (PDGFR), insulin-like growth factor (IGFR), nerve growth factor (NGFR), and fibroblast growth factor (FGF).

Preferably, the growth factor receptor antagonist to be used in this invention as a chemotherapeutic agent is an EGFR antagonist. In this specification, EGFR refers to the EGFR family of receptors. The family includes EGFR, which is also referred to in the literature as HER1; HER2, which is also referred to in the literature as Neu, c-erB-2, and p185erbB-2; HER3, which is also referred to in the literature as erbB-3; and HER4, which is also referred to in the literature as erbB-4. The specific member of the EGFR family of receptors that is also called EGFR will be referred to as EGFR/HER1. The EGFR antagonists can be cytostatic. Preferably, the EGFR antagonist is cytotoxic.

The EGFR antagonist may, for example, be an antibody. Antibodies may be made from the desired EGF receptor by methods that are well known in the art. The receptors are either commercially available, or can be isolated by well known methods. For example, methods for isolating and purifying EGFR are found in Spada, U.S. Pat. No. 5,646,153 starting at column 41, line 55. The method for isolating and purifying EGFR described in the Spada patent is incorporated herein by reference.

Suitable EGFR antibodies are also known in the art. For example, U.S. Pat. No. 4,943,533 describes a murine monoclonal antibody called 225 that binds to the EGF receptor. The patent is assigned to the University of California and licensed exclusively to ImClone Systems Incorporated. The 225 antibody is able to inhibit the growth of cultured EGFR-expressing in vivo and in vivo. See Masui et al., Cancer Res. 44, 5592–5598 (1986).

The 225 antibody is able to inhibit the growth of cultured EGFR/HER1-expressing tumor cells in vitro as well as in vivo when grown as xenografts in nude mice. See Masui et al., Cancer Res. 44, 5592–5598 (1986). More recently, a treatment regimen combining 225 plus doxorubicin or cisplatin exhibited therapeutic synergy against several well established human xenograft models in mice. Basalga et al., J. Natl. Cancer Inst. 85, 1327–1333 (1993).

Preferred EGFR antibodies are the chimerized, humanized, and single chain antibodies derived from the 225 antibody. These antibodies can be made from the 225 antibody, which is available from the ATCC. Alternatively, the various fragments needed to prepare the chimerized, humanized, and single chain 225 antibodies can be synthesized from the sequence provided in Wels et al. in Int. J. Cancer 60, 137–144 (1995). The chimerized 225 antibody (c225) can be made in accordance with the methods described above. Humanized 225 antibody can be prepared in accordance with the method described in example IV of PCT application WO 96/40210, which is incorporated herein by reference. Single chain 225 antibodies (Fv225) can be made in accordance with methods described by Wels et al. in Int. J. Cancer 60, 137–144 (1995) and in European patent application 502 812.

The sequences of the heavy chain hypervariable regions of the 225 antibody are as follows: CDR1: SEQ ID NO: 25 and 26; CDR2: SEQ ID NO: 27 and 28; and CDR3: SEQ ID NO: 29 and 30. The sequences of the light chain hypervariable regions are as follows: CDR1: SEQ ID NO: 31 and 32; CDR2: SEQ ID NO: 33 and 34; and CDR3: SEQ ID NO: 35 and 36.

Additionally, the EGFR antagonist may be a small molecule. Numerous small molecules have been described as being useful to inhibit EGFR.

For example, Spada et al., U.S. Pat. No. 5,656,655, discloses styryl substituted heteroaryl compounds that inhibit EGFR. The heteroaryl group is a monocyclic ring with one or two heteroatoms, or a bicyclic ring with 1 to about 4 heteroatoms, the compound being optionally substituted or polysubstituted. The compounds disclosed in U.S. Pat. No. 5,656,655 are incorporated herein by reference.

Spada et al., U.S. Pat. No. 5,646,153 discloses bis mono and/or bicyclic aryl heteroaryl, carbocyclic, and heterocarbocyclic compounds that inhibit EGFR. The compounds disclosed in U.S. Pat. No. 5,646,153 are incorporated herein by reference.

Bridges et al., U.S. Pat. No. 5,679,683 discloses tricyclic pyrimidine compounds that inhibit the EGFR. The compounds are fused heterocyclic pyrimidine derivatives described at column 3, line 35 to column 5, line 6. The description of these compounds at column 3, line 35 to column 5, line 6 is incorporated herein by reference.

Barker, U.S. Pat. No. 5,616,582 discloses quinazoline derivatives that have receptor tyrosine kinase inhibitory activity. The compounds disclosed in U.S. Pat. No. 5,616,582 are incorporated herein by reference.

Fry et al., Science 265, 1093–1095 (1994) discloses a compound having a structure that inhibits EGFR. The structure is shown in FIG. 1. The compound shown in FIG. 1 of the Fry et al. article is incorporated herein by reference.

Osherov et al., disclose tyrphostins that inhibit EGFR/HER1 and HER2. The compounds disclosed in the Osherov et al. article, and, in particular, those in Tables I, II, III, and IV are incorporated herein by reference.

Levitzki et al., U.S. Pat. No. 5,196,446, discloses heteroarylethenediyl or heteroarylethenediylaryl compounds that inhibit EGFR. The compounds disclosed in U.S. Pat. No. 5,196,446 from column 2, line 42 to column 3, line 40 are incorporated herein by reference.

Panek, et al., Journal of Pharmacology and Experimental Therapeutics 283, 1433–1444 (1997) disclose a compound identified as PD166285 that inhibits the EGFR, PDGFR, and FGFR families of receptors. PD166285 is identified as 6-(2,6-dichlorophenyl)-2-(4-(2-diethylaminoethoxy)phenylamino)-8-methyl-8H-pyrido(2,3-d)pyrimidn-7-one having the structure shown in FIG. 1 on page 1436. The compound described in FIG. 1 on page 1436 of the Panek et al. article is incorporated herein by reference VEGF Receptor Antagonists In one embodiment, the VEGF receptor antagonist binds specifically to an epitope on the extracellular domain of a VEGF receptor. The extracellular domain of a VEGF receptor is the ligand-binding domain. The ligand-binding domain may be found at either end of the receptor, but is normally found at the amino-terminal end.

Some examples of VEGF receptors include the protein tyrosine kinase receptors referred to in the literature as FLT-1, KDR and FLK-1. Unless otherwise stated or clearly suggested otherwise by context, this specification will follow the customary literature nomenclature of VEGF receptors. KDR will be referred to as the human form of a VEGF receptor having MW 180 kD (Terman et al., above). FLK-1 will be referred to as the murine homolog of KDR (Matthews et al., above). FLT-1 will be referred to as a form of VEGF receptor different from, but related to, the KDR/FLK-1 receptor. See Shibuya et al., above.

Other VEGF receptors include those that can be cross-link labeled with VEGF, or that can be co-immunoprecipitated with KDR. Some known forms of these VEGF receptors have molecular weights of approximately 170 KD, 150 KD, 130–135 KD, 120–125 KD and 85 KD. See, for example, Quinn et al. Proc. Nat'l. Acad. Sci 90, 7533–7537 (1993). Scher et al. J. Biol. Chem. 271, 5761–5767 (1996).

The VEGF receptor is usually bound to a cell, such as an endothelial cell. The VEGF receptor may also be bound to a non-endothelial cell, such as a tumor cell. Alternatively, the VEGF receptor may be free from the cell, preferably in soluble form.

The antagonists, e.g. antibodies, of the invention neutralize VEGF receptors. In this specification, neutralizing a receptor means inactivating the intrinsic kinase activity of the receptor to transduce a signal. A reliable assay for VEGF receptor neutralization is the inhibition of receptor phosphorylation.

The present invention is not limited by any particular mechanism of VEGF receptor neutralization. At the time of filing this application, the mechanism of VEGF receptor neutralization by antibodies was not well understood, and the mechanism followed by one antagonist is not necessarily the same as that followed by another antagonist. Some possible mechanisms include preventing binding of the VEGF ligand to the extracellular binding domain of the VEGF receptor, and preventing dimerization or oligomerization of receptors. Other mechanisms cannot, however, be ruled out.

Antibody VEGFR Antagonists

In one embodiment, the VEGFR antagonist is an antibody.

The monoclonal antibodies that specifically bind to the VEGF receptor may be produced by methods known in the art. These methods include the immunological method described by Kohler and Milstein in Nature 256, 495–497 (1975) and Campbell in "Monoclonal Antibody Technology, The Production and Characterization of Rodent and Human Hybridomas" in Burdon et al., Eds., Laboratory Techniques in Biochemistry and Molecular Biology, Volume 13, Elsevier Science Publishers, Amsterdam (1985); as well as by the recombinant DNA method described by Huse et al in Science 246, 1275–1281 (1989).

The antibodies of the invention may be prepared by immunizing a mammal with a soluble VEGF receptor. The soluble receptors may be used by themselves as immunogens, or may be attached to a carrier protein or to other objects, such as beads, i.e. sepharose beads. After the mammal has produced antibodies, a mixture of antibody-producing cells, such as the splenocytes, is isolated. Monoclonal antibodies may be produced by isolating individual antibody-producing cells from the mixture and making the cells immortal by, for example, fusing them with tumor cells, such as myeloma cells. The resulting hybridomas are preserved in culture, and express monoclonal antibodies, which are harvested from the culture medium.

The antibodies may also be prepared from VEGF receptors bound to the surface of cells that express the VEGF receptor. The cell to which the VEGF receptors are bound may be a cell that naturally expresses the receptor, such as a vascular endothelial cell. Alternatively, the cell to which the receptor is bound may be a cell into which the DNA encoding the receptor has been transfected, such as 3T3 cells.

The antibody may be prepared in any mammal, including mice, rats, rabbits, goats and humans. The antibody may be a member of one of the following immunoglobulin classes: IgG, IgM, IgA, IgD, or IgE, and the subclasses thereof, and preferably is an IgG1 antibody.

In one embodiment the antibody is a monoclonal antibody directed to an epitope of a VEGF receptor present on the surface of a cell. In another embodiment the monoclonal antibody is a rat IgG1 monoclonal antibody, specific for the murine VEGF receptor FLK-1, and produced by hybridoma DC-101. Hybridoma cell line DC-101 was deposited Jan. 26, 1994 with the American Type Culture Collection, designated ATCC HB 11534. In a preferred embodiment, the monoclonal antibody is directed to an epitope of a human FLT-1 receptor or to a human KDR receptor.

Functional Equivalents of Antibodies

The invention also includes functional equivalents of the antibodies described in this specification. Functional equivalents have binding characteristics comparable to those of the antibodies, and include, for example, chimerized, humanized and single chain antibodies as well as fragments thereof. Methods of producing such functional equivalents are disclosed in PCT Application WO 93/21319, European Patent Application No. 239,400; PCT Application WO 89/09622; European Patent Application 338,745; and European Patent Application EP 332,424.

Chimerized antibodies preferably have constant regions derived substantially or exclusively from human antibody constant regions and variable regions derived substantially or exclusively from the sequence of the variable region from a mammal other than a human. Humanized antibodies preferably have constant regions and variable regions other than the complement determining regions (CDRs) derived substantially or exclusively from the corresponding human antibody regions and CDRs derived substantially or exclusively from a mammal other than a human.

Suitable mammals other than a human include any mammal from which monoclonal antibodies may be made. Suitable examples of mammals other than a human include, for example a rabbit, rat, mouse, horse, goat, or primate. Mice are preferred.

Single chain antibodies (scFv) are polypeptides that consist of the variable region of the heavy chain of the antibody linked to the variable region of the light chain with or without an interconnecting linker. Thus, the scFv comprises the entire antibody combining site. These chains may be produced in bacteria, or in eukaryotic cells.

An example of a single chain antibody is p1C11. (See Example IX below.) P1C11 was shown to block VEGF- KDR interaction and inhibit VEGF-stimulated receptor phosphorylation and mitogenesis of HUVEC. This scFv binds both soluble KDR and cell surface-expressed KDR on HUVEC. The sequence p1C11 of is shown as SEQ ID No: 21.

The single chain antibodies described above can be built up into a chimerized or humanized antibody by methods known in the art; e.g., see example IX-3 below. The preferred chimerized scFv is chimerized p1C11, i.e. c-p1C11. Functional equivalents further include other fragments of antibodies that have the same, or binding characteristics comparable to, those of the whole antibody. Such fragments may contain one or both Fab fragments or the $F(ab')_2$ fragment. Preferably the antibody fragments contain all six complementarity-determining regions of the whole antibody, although fragments containing fewer than all of such regions, such as three, four or five CDRs, are also functional.

The antibodies of the invention and their functional equivalents may be or may combine members of any of the immunoglobulin classes. Examples of immunoglobulin classes include: IgG, IgM, IgA, IgD, or IgE, and the subclasses thereof.

Non-Antibody VEGFR Antagonists

In addition to the antibodies, or functional equivalents of antibodies, discussed above, the receptor antagonists useful in the present invention may also be other biological and small molecules, especially in connection with the treatments described above.

Biological molecules include all lipids and polymers of monosaccharides, amino acids and nucleotides having a molecular weight greater than 450. Thus, biological molecules include, for example, oligosaccharides and polysaccharides; oligopeptides, polypeptides, peptides, and proteins; and oligonucleotides and polynucleotides. Oligonucleotides and polynucleotides include, for example, DNA and RNA.

Biological molecules further include derivatives of any of the molecules described above. For example, derivatives of biological molecules include lipid and glycosylation derivatives of oligopeptides, polypeptides, peptides and proteins. Derivatives of biological molecules further include lipid derivatives of oligosaccharides and polysaccharides, e.g. lipopolysaccharides.

Any molecule that is not a biological molecule is considered in this specification to be a small molecule. Some examples of small molecules include organic compounds, organometallic compounds, salts of organic and organometallic compounds, saccharides, amino acids, nucleosides and nucleotides. Small molecules further include molecules that would otherwise be considered biological molecules, except their molecular weight is not greater than 450. Thus, small molecules may be lipids, oligosaccharides, oligopeptides, and oligonucleotides, and their derivatives, having a molecular weight of 450 or less.

It is emphasized that small molecules can have any molecular weight. They are merely called small molecules because they typically have molecular weights less than 450. Small molecules include compounds that are found in nature as well as synthetic compounds. Preferably, the small molecules inhibit the growth of both solid and non-solid tumor cells that express VEGF receptor tyrosine kinase.

Hennequin et al. in J. Med. Chem. 42, 5369–5389 (1999) disclose certain quinazolines, quinolines and cinnolines as being useful as inhibitors of VEGF receptors. See also Annie et al., Journal of Acquired Immune Deficiency Syndromes and Human Retrovirology 17, A41 (1998). The VEGF receptor inhibitors disclosed in the Hennequin et al. article are incorporated herein by reference.

Additionally, App et al. (U.S. Pat. No. 5,849,742) disclose small molecule derivatives of quinazoline, quinoxiline, substituted aniline, isoxazoles, acrylonitrile and phenylacrylonitrile compounds which act as tyrosine kinase inhibitors. The small molecules described by Hennequin et al., Annie et al., and App et al. are included in the present invention.

The administration of small molecule and biological drugs to human patients is accomplished by methods known in the art. Examples of such methods for small molecules are described in Spada, U.S. Pat. No. 5,646,153 at column 57, line 47 to column 59, line 67. This description of administering small molecules is incorporated herein by reference.

All molecules are intended to be covered by one or the other of the above definitions. For example, the molecule may comprise a biological molecule bonded to a small molecule.

UTILITY

A. Neutralizing VEGF Activation of VEGF Receptors:

Neutralization of VEGF activation of a VEGF receptor in a sample of endothelial or non-endothelial cells, such as tumor cells, may be performed in vitro or in vivo. Neutralizing VEGF activation of a VEGF receptor in a sample of VEGE-receptor expressing cells comprises contacting the cells with an anatagonist, e.g. an antibody, of the invention. The cells are contacted in vitro with the antagonist, e.g. the antibody, before, simultaneously with, or after, adding VEGF to the cell sample.

In vivo, an antagonist, e.g. an antibody, of the invention is contacted with a VEGF receptor by administration to a mammal. Methods of administration to a mammal include, for example, oral, intravenous, intraperitoneal, subcutaneous, or intramuscular administration.

This in vivo neutralization method is useful for inhibiting angiogenesis in a mammal. Angiogenesis inhibition is a useful therapeutic method, such as for preventing or inhibiting angiogenesis associated with pathological conditions such as tumor growth. Accordingly, the antagonists, e.g. the antibodies, of the invention are anti-angiogenic and anti-tumor immunotherapeutic agents.

The word mammal means any mammal. Some examples of mammals include pet animals, such as dogs and cats; farm animals, such as pigs, cattle, sheep, and goats; laboratory animals, such as mice and rats; primates, such as monkeys, apes, and chimpanzees; and humans.

VEGF receptors are found on some non-endothelial cells, such as tumor cells, indicating the unexpected presence of an autocrine and/or paracrine loop in these cells. The antagonists, e.g. the antibodies, of this invention are useful in neutralizing activity of VEGF receptors on such cells, thereby blocking the autocrine and/or paracrine loop, and inhibiting tumor growth.

The methods of inhibiting angiogenesis and of inhibiting pathological conditions such as tumor growth in a mammal comprise administering an effective amount of any one of the invention's antagonists, e.g. antibodies, including any of the functional equivalents thereof, systemically to a mammal, or directly to a tumor within the mammal. The mammal is preferably human. This method is effective for treating subjects with both solid tumors, preferably highly vascular tumors, and non-solid tumors.

The reduction of tumor growth includes the prevention or inhibition of the progression of a tumor, including cancerous and noncancerous tumors. The progression of a tumor includes the invasiveness, metastasis, recurrence and increase in size of the tumor. The reduction of tumor growth also includes the destruction of a tumor.

All types of tumors may be treated by the methods of the present invention. The tumors may be solid or non-solid.

Some examples of solid tumors that can be treated with the antagonists of the present invention include carcinomas, sarcomas, blastomas or gliomas. Some examples of such tumors include epidermoid tumors, squamous tumors, such as head and neck tumors, colorectal tumors, prostate tumors, breast tumors, lung tumors, including small cell and non-small cell lung tumors, pancreatic tumors, thyroid tumors, ovarian tumors, and liver tumors. Other examples include Kaposi's sarcoma, CNS neoplasms, neuroblastomas, capillary hemangioblastomas, meningiomas and cerebral metastases, melanoma, gastrointestinal and renal carcinomas and sarcomas, rhabdomyosarcoma, glioblastoma, preferably glioblastoma multiforme, and leiomyosarcoma. Examples of vascularized skin cancers for which the antagonists of this invention are effective include squamous cell carcinoma, basal cell carcinoma and skin cancers that can be treated by suppressing the growth of malignant keratinocytes, such as human malignant keratinocytes.

Some examples of non-solid tumors include leukemias, multiple myelomas and lymphomas. Some examples of leukemias include acute myelocytic leukemia (AML), chronic myelocytic leukemia (CML), acute lymphocytic leukemia (ALL), chronic lymphocytic leukemia (CLL), erythrocytic leukemia or monocytic leukemia. Some examples of lymphomas include lymphomas associated with Hodgkin's disease and Non-Hodgkin's disease.

Experimental results described later demonstrate that antibodies of the invention specifically block VEGF induced phosphorylation of a mouse extracellular FLK-1/intracellular fms chimeric receptor expressed in transfected 3T3 cells. The antibodies had no effect on a fully stimulated chimeric extracellular fms/intracellular FLK-2 receptor by CSF-1. In vivo studies also described below show that the antibodies were able to significantly inhibit tumor growth in nude mice.

A cocktail of VEGF receptor antagonists, e.g. monoclonal antibodies, provides an especially efficient treatment for inhibiting the growth of tumor cells. The cocktail may include as few as 2, 3 or 4 antibodies, and as many as 6, 8 or 10 antibodies.

Preventing or inhibiting angiogenesis is also useful to treat non-neoplastic pathologic conditions characterized by excessive angiogenesis, such as neovascular glaucoma, proliferative retinopathy including proliferative diabetic retinopathy, macular degeneration, hemangiomas, angiofibromas, and psoriasis.

B. Using the Antagonists, e.g. Antibodies, of the Invention to Isolate and Purify the VEGF Receptor The antagonists, e.g. antibodies, of the present invention may be used to isolate and purify the VEGF receptor using conventional methods such as affinity chromatography (Dean, P. D. G. et al., Affinity Chromatography: A Practical Approach, IRL Press, Arlington, Va. (1985)). Other methods well known in the art include magnetic separation with antibody-coated magnetic beads, "panning" with an antibody attached to a solid matrix, and flow cytometry.

The source of the VEGF receptor is typically vascular cells, and especially vascular endothelial cells, that express the VEGF receptor. Suitable sources of vascular endothelial cells are blood vessels, such as umbilical cord blood cells, especially, human umbilical cord vascular endothelial cells (HUVEC).

The VEGF receptors may be used as starting material to produce other materials, such as antigens for making additional monoclonal and polyclonal antibodies that recognize and bind to the VEGF receptor or other antigens on the surface of VEGF-expressing cells.

C. Using the Antagonists, e.g. Antibodies, of the Invention to Isolate and Purify FLK-1 Positive Tumor Cells The antagonists, e.g. antibodies, of the present invention may be used to isolate and purify FLK-1 positive tumor cells, i.e., tumor cells expressing the FLK-1 receptor, using conventional methods such as affinity chromatography (Dean, P. D. G. et al., Affinity Chromatography: A Practical Approach, IRL Press, Arlington, Va. (1985)). Other methods well known in the art include magnetic separation with antibody-coated magnetic beads, cytotoxic agents, such as complement, conjugated to the antibody, "panning" with an antibody attached to a solid matrix, and flow cytometry.

D. Monitoring Levels of VEGF and VEGF Receptors in vitro or in vivo

The antagonists, e.g. antibodies, of the invention may be used to monitor levels of VEGF or VEGF receptors in vitro or in vivo in biological samples using standard assays and methods known in the art. Some examples of biological samples include bodily fluids, such as blood. Standard assays involve, for example, labeling the antibodies and conducting standard immunoassays, such as radioimmunoassays, as is well know in the art.

Preparation of Receptor Immunogens

A receptor may be used as an immunogen to raise an antibody of the invention. The receptor peptide may be obtained from natural sources, such as from cells that express the receptors. For example, the VEGF receptor peptide may be obtained from vascular endothelial cells. Alternatively, synthetic receptor peptides may be prepared using commercially available machines. In such an embodiment, the VEGF receptor amino acid sequence can be provided by, for example, Shibuya M. et al., Oncogene 5, 519–524 (1990) for FLT-1; PCT/US92/01300 and Terman et al., Oncogene 6:1677–1683 (1991) for KDR; and Matthews W. et al. Proc. Natl. Acad. Sci. USA, 88:9026–9030 (1991) for FLK-1.

As a further alternative, DNA encoding a receptor, such as a cDNA or a fragment thereof, may be cloned and expressed and the resulting polypeptide recovered and used as an immunogen to raise an antibody of the invention. For example, in order to prepare the VEGF receptors against which the antibodies are made, nucleic acid molecules that encode the VEGF receptors of the invention, or portions thereof, especially the extracellular portions thereof, may be inserted into known vectors for expression in host cells using standard recombinant DNA techniques, such as those described below. Suitable sources of such nucleic acid molecules include cells that express VEGF receptors, i.e. vascular endothelial cells.

Preparation of Equivalents

Equivalents of antibodies are prepared by methods known in the art. For example, fragments of antibodies may be prepared enzymatically from whole antibodies.

Preferably, equivalents of antibodies are prepared from DNA encoding such equivalents. DNA encoding fragments of antibodies may be prepared by deleting all but the desired portion of the DNA that encodes the full length antibody.

DNA encoding chimerized antibodies may be prepared by recombining DNA encoding human constant regions, derived substantially or exclusively from the corresponding human antibody regions, and DNA encoding variable regions, derived substantially or exclusively from the sequence of the variable region of a mammal other than a human. DNA encoding humanized antibodies may be prepared by recombining DNA encoding constant regions and variable regions other than the complementarity determining regions (CDRs), derived substantially or exclusively from the corresponding human antibody regions, and DNA encoding CDRs, derived substantially or exclusively from a mammal other than a human.

Suitable sources of DNA molecules that encode fragments of antibodies include cells, such as hybridomas, that express the full length antibody. The fragments may be used by themselves as antibody equivalents, or may be recombined into equivalents, as described above.

The DNA deletions and recombinations described in this section may be carried out by known methods, such as those described in the published patent applications listed above in the section entitled "Functional Equivalents of Antibodies" and/or other standard recombinant DNA techniques, such as those described below.

Standard Recombinant DNA Techniques

Standard recombinant DNA techniques useful in carrying out the present invention are described in Sambrook et al., "Molecular Cloning," Second Edition, Cold Spring Harbor Laboratory Press (1987) and by Ausubel et al. (Eds) "Current Protocols in Molecular Biology," Green Publishing Associates/Wiley-Interscience, New York (1990).

Briefly, a suitable source of cells containing nucleic acid molecules that express the desired DNA, such as an antibody, antibody equivalent or VEGF receptor, is selected. See above.

Total RNA is prepared by standard procedures from a suitable source. The total RNA is used to direct cDNA synthesis. Standard methods for isolating RNA and synthesizing cDNA are provided in standard manuals of molecular biology such as, for example, those described above.

The cDNA may be amplified by known methods. For example, the cDNA may be used as a template for amplification by polymerase chain reaction (PCR); see Saiki et al., Science, 239, 487 (1988) or Mullis et al., U.S. Pat. No. 4,683,195. The sequences of the oligonucleotide primers for the PCR amplification are derived from the known sequence to be amplified. The oligonucleotides are synthesized by methods known in the art. Suitable methods include those described by Caruthers in Science 230, 281–285 (1985).

A mixture of upstream and downstream oligonucleotides are used in the PCR amplification. The conditions are optimized for each particular primer pair according to standard procedures. The PCR product is analyzed, for example, by electrophoresis for cDNA having the correct size, corresponding to the sequence between the primers.

Alternatively, the coding region may be amplified in two or more overlapping fragments. The overlapping fragments are designed to include a restriction site permitting the assembly of the intact cDNA from the fragments.

In order to isolate the entire protein-coding regions for the VEGE receptors, for example, the upstream PCR oligonucleotide primer is complementary to the sequence at the 5' end, preferably encompassing the ATG start codon and at least 5–10 nucleotides upstream of the start codon. The downstream PCR oligonucleotide primer is complementary to the sequence at the 3' end of the desired DNA sequence. The desired DNA sequence preferably encodes the entire extracellular portion of the VEGF receptor, and optionally encodes all or part of the transmembrane region, and/or all or part of the intracellular region, including the stop codon.

The DNA to be amplified, such as that encoding antibodies, antibody equivalents, or VEGF receptors, may also be replicated in a wide variety of cloning vectors in a wide variety of host cells. The host cell may be prokaryotic or eukaryotic.

The vector into which the DNA is spliced may comprise segments of chromosomal, non-chromosomal and synthetic DNA sequences. Some suitable prokaryotic cloning vectors include plasmids from E. coli, such as colE1, pCR1, pBR322, pMB9, pUC, pKSM, and RP4. Prokaryotic vectors also include derivatives of phage DNA such as M13 and other filamentous single-stranded DNA phages.

A preferred vector for cloning nucleic acid encoding the VEGF receptor is the Baculovirus vector.

The vector containing the DNA to be expressed is transfected into a suitable host cell. The host cell is maintained in an appropriate culture medium, and subjected to conditions under which the cells and the vector replicate. The vector may be recovered from the cell. The DNA to be expressed may be recovered from the vector.

Expression and Isolation of Antibodies, Antibody Equivalents, or Receptors

The DNA to be expressed, such as that encoding antibodies, antibody equivalents, or receptors, may be inserted into a suitable expression vector and expressed in a suitable prokaryotic or eucaryotic host cell.

For example, the DNA inserted into a host cell may encode the entire extracellular portion of the VEGF receptor, or a soluble fragment of the extracellular portion of the VEGF receptor. The extracellular portion of the VEGF receptor encoded by the DNA is optionally attached at either, or both, the 5' end or the 3' end to additional amino acid sequences. The additional amino acid sequences may be attached to the VEGF receptor extracellular region in nature, such as the leader sequence, the transmembrane region and/or the intracellular region of the VEGF receptor. The additional amino acid sequences may also be sequences not attached to the VEGF receptor in nature. Preferably, such additional amino acid sequences serve a particular purpose, such as to improve expression levels, secretion, solubility, or immunogenicity.

Vectors for expressing proteins in bacteria, especially E. coli, are known. Such vectors include the PATH vectors described by Dieckmann and Tzagoloff in J. Biol. Chem. 260, 1513–1520 (1985). These vectors contain DNA sequences that encode anthranilate synthetase (TrpE) followed by a polylinker at the carboxy terminus. Other expression vector systems are based on beta-galactosidase (pEX); lambda $P_L$; maltose binding protein (pMAL); and glutathione S-transferase (pGST)-see Gene 67, 31 (1988) and Peptide Research 3, 167 (1990).

Vectors useful in yeast are available. A suitable example is the $2\mu$ plasmid.

Suitable vectors for expression in mammalian cells are also known. Such vectors include well-known derivatives of SV-40, adenovirus, retrovirus-derived DNA sequences and shuttle vectors derived from combination of functional mammalian vectors, such as those described above, and functional plasmids and phage DNA.

Further eukaryotic expression vectors are known in the art (e.g., P. J. Southern and P. Berg, J. Mol. Appl. Genet. 1, 327–341 (1982); S. Subramani et al, Mol. Cell. Biol. 1, 854–864 (1981); R. J. Kaufmann and P. A. Sharp, "Amplification And Expression of Sequences Cotransfected with a Modular Dihydrofolate Reductase Complementary DNA Gene," J. Mol. Biol. 159, 601–621 (1982); R. J. Kaufmann and P. A. Sharp, Mol. Cell. Biol. 159, 601–664 (1982); S. I. Scahill et al, "Expression And Characterization Of The Product Of A Human Immune Interferon DNA Gene In Chinese Hamster Ovary Cells," Proc. Natl. Acad. Sci. USA 80, 4654–4659 (1983); G. Urlaub and L. A. Chasin, Proc. Natl. Acad. Sci. USA 77, 4216–4220, (1980).

The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters or SV40, and other sequences known to control the expression of genes of prokaryotic or eukaryotic cells and their viruses or combinations thereof.

Vectors containing the control signals and DNA to be expressed, such as that encoding antibodies, antibody equivalents, or VEGF receptors, are inserted into a host cell for expression. Some useful expression host cells include well-known prokaryotic and eukaryotic cells. Some suitable prokaryotic hosts include, for example, E. coli, such as E. coli SG-936, E. coli HB 101, E. coli W3110, E. coli X1776, E. coli X2282, E. coli DHI, and E. coli MRC1, Pseudomonas, Bacillus, such as Bacillus subtilis, and Streptomyces. Suitable eukaryotic cells include yeast and other fungi, insect, animal cells, such as COS cells and CHO cells, human cells and plant cells in tissue culture.

Following expression in a host cell maintained in a suitable medium, the polypeptide or peptide to be expressed, such as that encoding antibodies, antibody equivalents, or VEGF receptors, may be isolated from the medium, and purified by methods known in the art. If the polypeptide or peptide is not secreted into the culture medium, the host cells are lysed prior to isolation and purification.

EXAMPLES

The Examples which follow are set forth to aid in understanding the invention but are not intended to, and should not be construed to, limit its scope in any way. The Examples do not include detailed descriptions of conventional methods, such as those employed in the construction of vectors and plasmids, the insertion of genes encoding polypeptides into such vectors and plasmids, or the introduction of plasmids into host cells. Such methods are well known to those of ordinary skill in the art and are described in numerous publications including Sambrook, J., Fritsch, E. F. and Maniatis, T. (1989) Molecular Cloning: A Laboratory Manual, 2nd edition, Cold Spring Harbor Laboratory Press.

Example I

Cell Lines and Media

NIH 3T3 cells were obtained from the American Type Culture Collection (Rockville Md.). The C441 cell line was constructed by transfecting 3T3 cells with the chimeric receptor mouse FLK-1/human fms. 10A2 is a 3T3 transfectant containing the chimeric receptor human fms/mouse FLK-2, the isolation and characterization of which has been described (Dosil, M. et al., Mol. Cell. Biol. 13:6572–6585 (1993)). Cells were routinely maintained in Dulbecco's modified Eagle's medium (DME) supplemented with 10% calf serum (CS), 1 mM L-glutamine, antibiotics, and 600 µg/ml G418 (Geneticin; Sigma, St Louis Mo.).

A glioblastoma cell line, GBM-18, was maintained in DME supplemented with 5% calf serum, 1 mM L-glutamine, and antibiotics.

A stable 3T3 line secreting the soluble chimeric protein, mouse FLK-1:SEAPs (secretory alkaline phosphastase), was generated and maintained in DMEM and 10% calf serum. Conditioned media was collected. Soluble FLK-1:SEAP is isolated from the conditioned media.

Example II

Isolation of Monoclonal Antibodies

Example II-1

Rat Anti Mouse FLK-1 Monoclonal Antibody DC-101 (IgG1)

Lewis rats (Charles River Labs) were hyperimmunized with an immune complex consisting of the mouse FLK-1:SEAPs soluble receptor, a rabbit anti-alkaline phosphatase polyclonal antibody and Protein-G sepharose beads. The animals received 7 intraperitoneal injections of this complex spread over three months (at days 0, 14, 21, 28, 49, 63, 77). At various times, the animals were bled from the tail vein and immune sera screened by ELISA for high titer binding to mFLK-1: SEAPs. Five days after the final injection, rats were sacrificed and the spleens aseptically removed. Splenocytes were washed, counted, and fused at a 2:1 ratio with the murine myeloma cell line NS1. Hybridomas were selected in HAT medium and colonies screened by ELISA for specific binding to mFLK-1:SEAPs but not the SEAPs protein. A number of positive hybridomas were expanded and cloned three times by limiting dilution. One subclone, designated DC-101, was further characterized.

Example II-2

Mouse Anti Mouse FLK-1 Monoclonal Antibodies Mab 25 and Mab 73

Murine anti-FLK-1 monoclonal antibodies (Mabs) were produced using a similar protocol as that employed for DC-101. Briefly, mice were injected with a complex of FLK-1/SEAP soluble receptor bound to either an anti-SEAP-Protein/A Sepharose complex or wheat germ agglutinin Sepharose from conditioned medium of transfected NIH 3T3 cell. Mice were hyperimmunized at periodic intervals over a 6 month period. Immune splenocytes were pooled and fused with the murine myeloma cell line, NSI. Hybridomas were selected in HAT medium and following incubation, colonies were screened for mouse Mab production. Unlike the protocol employed for DC-101, positive supernatants were initially screened for binding to the FLK-1/fms receptor captured from C441 cell lysates on ELISA plates coated with a peptide generated polyclonal antibody against the C-terminal region of fms. Reactive Mabs were then assayed by ELISA for binding to intact C441 cells and to purified FLK-1/SEAP versus SEAP alone. The supernatants from hybridomas showing binding to C441 and reactivity with FLK-1/SEAP but not SEAP were expanded, grown in ascites, and purified (EZ-PREP, Pharmacia). Purified Mabs were subjected to assays on C441 cells to determine their cell surface binding by FACS and their ability to inhibit VEGF induced activation of FLK-1/fms in phosphorylation assays. The results of these studies led to the cloning of Mabs 25 and 73 (isotype IgG1) for further characterization based on their capabilities to bind specifically to FLK-1 and block receptor activation at levels comparable to that observed for DC-101.

Example III
Assays

Example III-1
ELISA Methods

Antibodies were screened by a solid state ELISA in which the binding characteristics of the various mAbs to FLK-1:SEAP and SEAP protein were compared. Microtiter plates were coated with 50–100 ng/well of either FLK-1:SEAP or AP in pH9.6 carbonate buffer overnight at 4° C. Plates were blocked with phosphate buffered saline supplemented with 10% new born calf serum (NB10) for one hour at 37° C. Hybridoma supernatants or purified antibodies were added to the plates for two hours at 37° C. followed by goat anti-rat IgG conjugated to horseradish peroxidase (Tago) added for an additional hour at 37° C. After extensive washing, TMB (Kirkegaard and Perry, Gaithersburg Md.) plus hydrogen peroxide was added as the chromogen and the plates read at 450 nm in an ELISA reader.

Example III-2
Isotyping

Isotyping of the various monoclonal antibodies was done as previously described (Songsakphisarn, R. and Goldstein, N. I., Hybridoma 12: 343–348, 1993) using rat isotype specific reagents (Zymed Labs, South San Francisco Calif.).

Example III-3
Phosphorylation, Immunoprecipitation and Immunoblot Assays

The phosphorylation assays and Western blot analysis with C441 and 10A2 cells were performed as previously described (Tessler et al., 1994) with some modifications. Briefly, cells were grown to 90% confluency in DME-10% CS and then serum starved in DME-0.5% CS for 24 hours prior to experimentation. HUVEC cells were grown to subconfluence in EGM basal media. For neutralization assays, cells were stimulated with various concentrations of the appropriate ligand under serum free conditions (DME -0.1% BSA) in the presence and absence of mAb DC-101 for 15 minutes at room temperature. The ligands, VEGF and CSF-1, were assayed at concentrations of 10–80 ng/ml and 20–40 ng/ml, respectively. Monoclonal antibodies were assayed at concentrations ranging from 0.5 µg/ml to 10 µg/ml. To evaluate the effects of mAb DC-101 on the VEGF induced activation of the FLK-1-fms receptor, antibody was either added simultaneously (competitive inhibition) or pre-bound to cells for 15 minutes at room temperature prior to the addition of ligand. Cells incubated in serum free medium in the absence and presence of DC-101 served as controls for receptor autophosphorylation in the absence of ligand and the presence of antibody, respectively. A control cell line expressing the fms/FLK-2 chimeric receptor (10A2) was starved and stimulated with 20 and 40 ng/ml CSF-1 and assayed in the presence and absence of 5 µg/ml DC-101.

Following stimulation, monolayers were washed with ice cold PBS containing 1 mM sodium orthovanadate. Cells were then lysed in lysis buffer (20 mM Tris-HCl, pH 7.4, 1% Triton X-100, 137 mM NaCl, 10% glycerol, 10 mM EDTA, 2 mM sodium orthovanadate, 100 mM NaF, 100 mM sodium pyrophosphate, 5 mM Pefabloc (Boehringer Mannheim Biochemicals, Indianapolis Ind.), 100 µg aprotinin and 100 µ/ml leupeptin) and centrifuged at 14000×g for 10 minutes. Protein was immunoprecipitated from cleared lysates of transfected cells using polyclonal antibodies generated to peptides corresponding to the C-terminal region of the human fms receptor (Tessler et al., J. Biol. Chem. 269, 12456–12461, 1994) or the murine FLK-2 interkinase domain (Small et al., Proc. Natl. Acad. Sci. USA, 91, 459–463, 1994) coupled to Protein A Sepharose beads. Where indicated, immunoprecipitations with DC-101 or irrelevant rat IgG were performed with 10 µg of antibody coupled to Protein G beads. The beads were then washed once with 0.2% Triton X-100, 10 mM Tris-HCl pH8.0, 150 mM NaCl, 2 mM EDTA (Buffer A), twice with Buffer A containing 500 mM NaCl and twice with Tris-HCl, pH 8.0. Drained beads were mixed with 30 µl in 2×SDS loading buffer and subjected to SDS PAGE in 4–12% gradient gels (Novex, San Diego Calif.). After electrophoresis, proteins were blotted to nitrocellulose filters for analysis. Filters were blocked overnight in blocking buffer (50 mM Tris-HCl, pH 7.4, 150 mM NaCl (TBS) containing 5% bovine serum albumin and 10% nonfat dried milk (Biorad, Calif.). To detect phosphorylated receptor, blots were probed with a monoclonal antibody directed to phosphotyrosine (UBI, Lake Placid, N.Y.) in blocking buffer for 1 hour at room temperature. Blots were then washed extensively with 0.5× TBS containing 0.1% Tween-20 (TBS-T) and incubated with goat anti-mouse Ig conjugated to horseradish peroxidase (Amersham). Blots were washed with TBS and incubated for 1 minute with a chemiluminescence reagent (ECL, Amersham). Anti-phosphotyrosine reacting with phosphorylated proteins was detected by exposure to a high performance luminescence detection film (Hyperfilm-ECL, Amersham) for 0.5 to 10 minutes.

To detect FLK-1/fms in C441 cells receptor levels, blots were stripped according to manufacturer's protocols (Amersham) and reprobed with the anti-fms rabbit polyclonal antibody.

Example III-4
Flow Cytometer Binding Assays

C441 cells were grown to near confluency in 10 cm plates. Cells were removed with a non-enzymatic dissociation buffer (Sigma), washed in cold serum free medium and resuspended in Hanks balanced salt solution supplemented with 1% BSA (HBSS-BSA) at a concentration of 1 million cells per tube. Monoclonal Ab DC-101 or an isotype matched irrelevant antibody anti FLK-2 23H7 was added at 10 µg per tube for 60 minutes on ice. After washing, 5 µl of goat anti-mouse IgG conjugated to FITC (TAGO) was added for an additional 30 minutes on ice. Cells were washed three times, resuspended in 1 ml of HBSS-BSA, and analyzed on a Coulter Epics Elite Cytometer. Non-specific binding of the fluorescent secondary antibody was determined from samples lacking the primary antibody.

Example III-5
Binding Assays to Intact Cells

Assays with C441 cells were performed with cells grown to confluency in 24 well dishes. HUVEC cells were grown to confluency in 6 well dishes. Monolayers were incubated at 4° C. for 2 hours with various amounts of mAb DC-101 in binding buffer (DMEM, 50 Mm HEPES pH 7.0, 0.5% bovine serum albumin). Cells were then washed with cold phosphate buffered saline (PBS) and incubated with a secondary anti-rat IgG antibody conjugated with biotin at a final concentration of 2.5 µg/ml. After 1 hour at 4° C. cells were washed and incubated with a streptavidin-horse radish peroxidase complex for 30 minutes at 4° C. Following washing, cell-bound antibody was determined by measuring the absorbance at 540 nm obtained with a colormetric detection system (TMB, Kirkegaard and Perry). The OD 540 nm of the secondary antibody alone served as the control for non-specific binding.

Example III-6

Cell Proliferation Assays

Mitogenic assays were performed using the Cell Titer 96 Non Radioactive Cell Proliferation Assay Kit (Promega Corp., Madison, Wis.). In this assay proliferation is measured color metrically as the value obtained from the reduction of a tetrazolium salt by viable cells to a formazan product. Briefly, HUVEC cells were grown in 24 well gelatin-coated plates in EGM basal media at 1000 cells/well. After a 48-hour incubation various components were added to the wells. VEGF was added at 10 ng/ml to the media in the presence and absence of 1 μg/ml of mAb DC-101. Where indicated, heparin (Sigma) was added to a final concentration of 1 μg/ml. Cells were then incubated for an additional 3 days. To measure cell growth, a 20 μl aliquot of tetrazolum dye was added to each well and cells were incubated for 3 hrs at 37° C. Cells were solubilized and the absorbance (OD570) of the formazan product was measured as a quantitation of proliferation.

Example IV

In vitro Activity Assays

Example IV-1

Murine Anti-FLK-1 Mabs 25 and 73 Elicit a Specific Neutralization of VEGF Induced Activation of the FLK-1/fms Receptor Assays were performed with immunoprecipitated FLK/fms and PDGF receptors from equal concentrations of the FLK-1/fms transfected 3T3 cell line, C441 whereas the human EGFR was immunoprecipitated from the tumor cell line, KB. Cells were stimulated with RPMI-0.5% BSA containing 20 ng/ml VEGF (FLK-1/fms), DMEM-10% calf serum (PDGFR), or 10 ng/ml EGF (EGFR), in the presence and absence of 10 μg/ml of the murine anti-FLK-1 Mabs, 25 and 73. Following stimulation, cells were washed with PBS-1 mM sodium orthovanadate and lysed. FLK-1/fms and PDGFR were immunoprecipitated from lysates with peptide generated polyclonal antibodies against the C-terminal region of the c-fms (IM 133) and the PDGF (UBI) receptors, respectively. EGFR was immunoprecipitated with a Mab (C225) raised against the N-terminal region of the human receptor. Immunoprecipitated lystates were subjected to SDS polyacrylamide electrophoresis followed by western blotting. Blots were probed with an anti-PTyr Mab (UBI) to detect receptor activation. Receptor neutralization of stimulated cells was assessed relative to an irrelevant Mab and the unstimulated control.

Example IV-2

Detection of the FLK-1/fms Receptor by Western Blotting Using Mab 25 and Mab 73 as Probes Receptor was detected by the murine anti-FLK-1 Mabs on western blots of the FLK-1/fms receptor immunoprecipiated by a peptide generated polyclonal antibody against the C-terminal region of the c-fms receptor from lysated prepared from equal concentrations of transfected 3T3 cell line C441. Following analysis by SDS gel electrophoresis and western blotting, the blot was divided into four parts and each section was probed with 50 μg/ml of the anti-FLK-1 Mabs 25 and 73. Blots were then stripped and reprobed with the anti-fms polyclonal antibody to verify that the bands detected by each Mab represented the FLK-1/fms receptor.

Example IV-3

Detection of Activated KDR from VEGF Stimulated HUVEC and OVCAR-3 Cells by Immunoprecipiation with Anti-FLK-1 Mabs Proteins were immunoprecipitated by different antibodies from a lysate of freshly isolated HUVEC. Prior to lysis, cells were stimulated with 20 ng/ml VEGF for 10 minutes at room temperature in RPMI-0.5% BSA and washed with PBS containing 1 mM sodium orthovanadate. Individual immunoprecipitations were performed with equal volumes of lysate and then subjected to SDS polyacrylamide electrophoresis followed by western blotting. The blot was probed initially with an anti-PTyr Mab (UBI) and then sequentially stripped and reprobed with a peptide generated polyclonal antibody against the interkinase of FLK-1/KDR (IM 142), followed by a polyclonal antibody against the C-terminal region of FLT-1 (Santa Cruz Biotechnology, Inc). The immunoprecipitations were performed with an irrelevant rat Mab, 23H7, an irrelevant mouse Mab, DAB 8, versus the anti-FLK-1 Mabs, DC-101, 73, 25 and an anti-FLK-1/KDR polyclonal antibody, IM 142. In some cases blots were stripped and reprobed with the anti-FLK-1 Mabs 73 and 25 to detect cross reactive bands.

A similar protocol was employed to detect KDR receptor form(s) in the ovarian carcinoma cell line OVCAR-3.

Example V

Activity of Antibodies

Example V-1

ELISA and Immunoprecipitation with DC-101

Rat IgG1 monoclonal antibody DC-101 was found to be specific for the murine tyrosine kinase receptor FLK-1. ELISA data showed that the antibody bound to purified FLK-1:SEAP but not alkaline phosphatase or other receptor tyrosine kinases such as FLK-2. As seen in FIG. 1, DC-101 immunoprecipitates murine FLK-1: SEAPS but not SEAPS alone.

Example V-2

Inhibition of Flk-1 Receptor Phosphorylation with DC-101

Figure 2A:
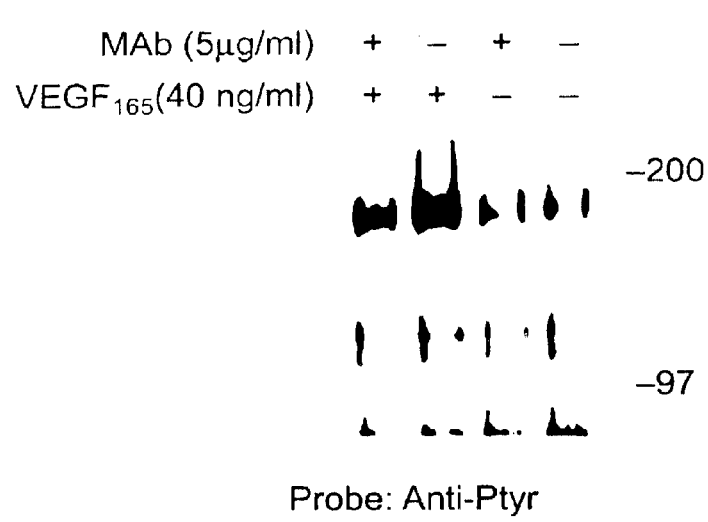
FIGS. 2a and 2b.
Figure 2B:
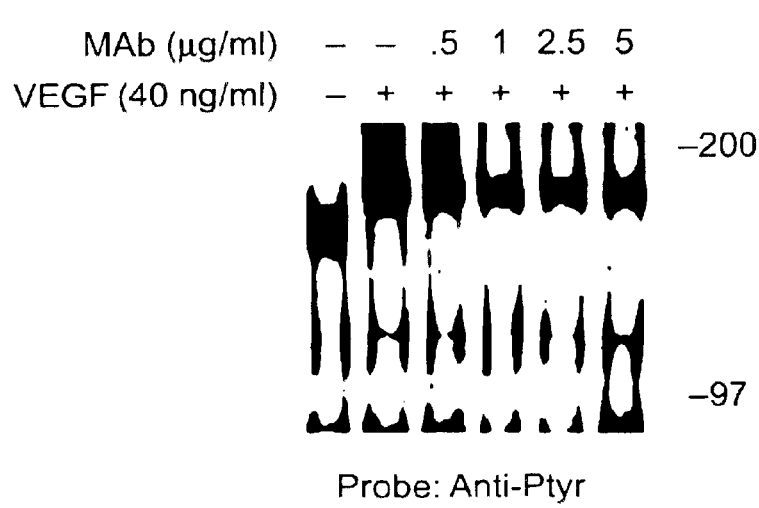
Figure 3A:
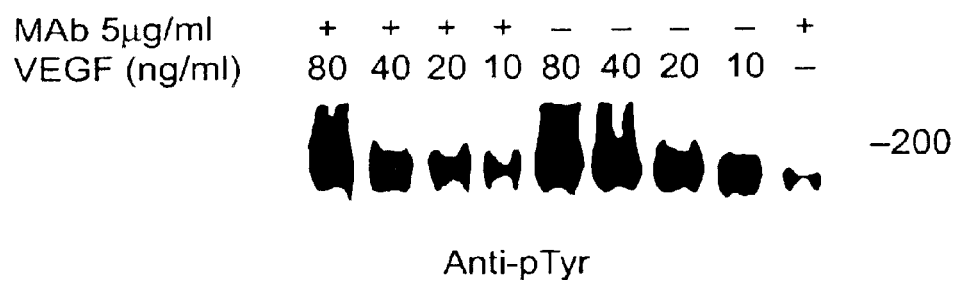
FIGS. 3a and 3b.
Figure 3B:
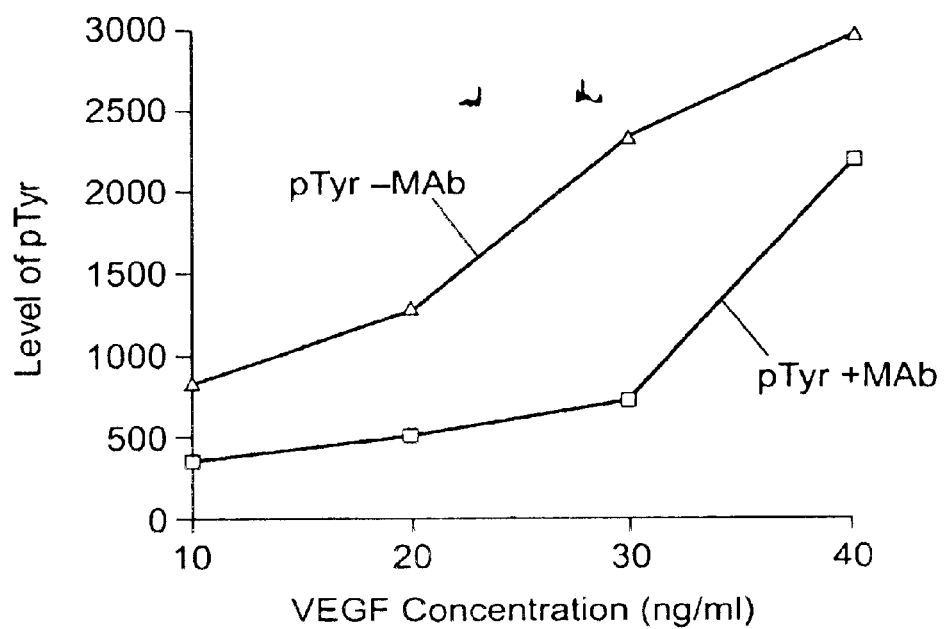

Experiments were then performed to determine whether DC-101 could neutralize phosphorylation of FLK-1 in C441 cells by its cognate ligand, $VEGF_{165}$. In these studies, monoclonal antibody and VEGF were added simultaneously to monolayers for 15 minutes at room temperature. These conditions were designed to determine the competitive effects (competitive inhibition) of the antibody on receptor/ligand binding. The results of these assays, shown in FIG. 2a, indicate that $VEGF_{165}$ induced phosphorylation of the FLK-1/fms receptor was markedly reduced when cells were assayed in the presence of DC-101. In addition, these data suggest that the Mab competes with $VEGF_{165}$ to prevent a full activation of receptor by ligand. To determine the sensitivity of the VEGF-FLK-1 interaction to inhibition by DC-101, C441 cells were assayed at maximal stimulatory concentrations of $VEGF_{165}$ (40 ng/ml) combined with varying levels of the antibody. The results of these Mab titrations are shown in FIG. 2b. A marked decrease in the phosphorylation of FLK-1 by $VEGF_{165}$ was observed when DC-101 was included at concentrations greater than 0.5 μg/ml. These data show that relatively low concentrations of antibody (<1 μg/ml) are sufficient to inhibit receptor activation by ligand. At 5 μg/ml the antibody is able to neutralize $VEGF_{165}$ stimulation of FLK-1 in the presence of excess ligand at 80 ng/ml (FIGS. 3a and 3b). As a control, the effect of DC-101 was tested on the fully stimulated fins/FLK-2 receptor (10A2 cell line) using CSF-1. Under these conditions, DC-101 showed no effect on receptor activation.

Example V-3
Inhibition Studies with DC-101

Figure 4:
FIG. 4: Inhibition of VEGF-FLK-1/fms activation by prebound mAb DC-101. C441 cells were stimulated with the concentrations of VEGF indicated in the absence (Lanes 3 and 4) and presence (Lanes 5 and 6) of DC-101. Unstimulated cells (Lanes 1 and 2) serve as controls. MAb was assayed using two sets of conditions. For P, cells were prebound with Mab followed by stimulation with VEGF for 15 minutes at room temperature. For C, MAb and ligand were added simultaneously and assayed as above.

The extent and specificity of Mab inhibition was further assessed by studies in which DC-101 was preincubated with cells before the addition of ligand to allow maximal interaction of antibody with receptor. In these experiments, monolayers were incubated with 5 µg/ml of DC-101, a rat anti-FLK-2 Mab (2A13) prepared by conventional techniques (ImClone, N.Y.), and control rat IgGI (Zymed Labs) for 15 minutes at room temperature prior to the addition of 40 ng/ml of $VEGF_{165}$ for an additional 15 minutes. For comparison, assays were run in which DC-101 and $VEGF_{165}$ were added simultaneously (competitive inhibition). The results of these studies (FIG. 4) show that preincubation of the anti-FLK-1 monoclonal antibody with FLK-1/fms transfected cells completely abrogates receptor activation by $VEGF_{165}$. Similar results were observed using $VEGF_{121}$ for stimulation. While phosphorylation of FLK-1 by VEGF is not affected by the addition of irrelevant isotype matched rat antibodies, the reactivity of the same blot probed with the anti-fms polyclonal antibody shows an equal level of receptor protein per lane. These data indicate that the inhibition of phosphorylation observed with DC-101 was due to the blockage of receptor activation rather than a lack of receptor protein in the test samples.

Example V-4
Binding of DC-101 to C441 Cells by FACS Analysis

Figure 6:
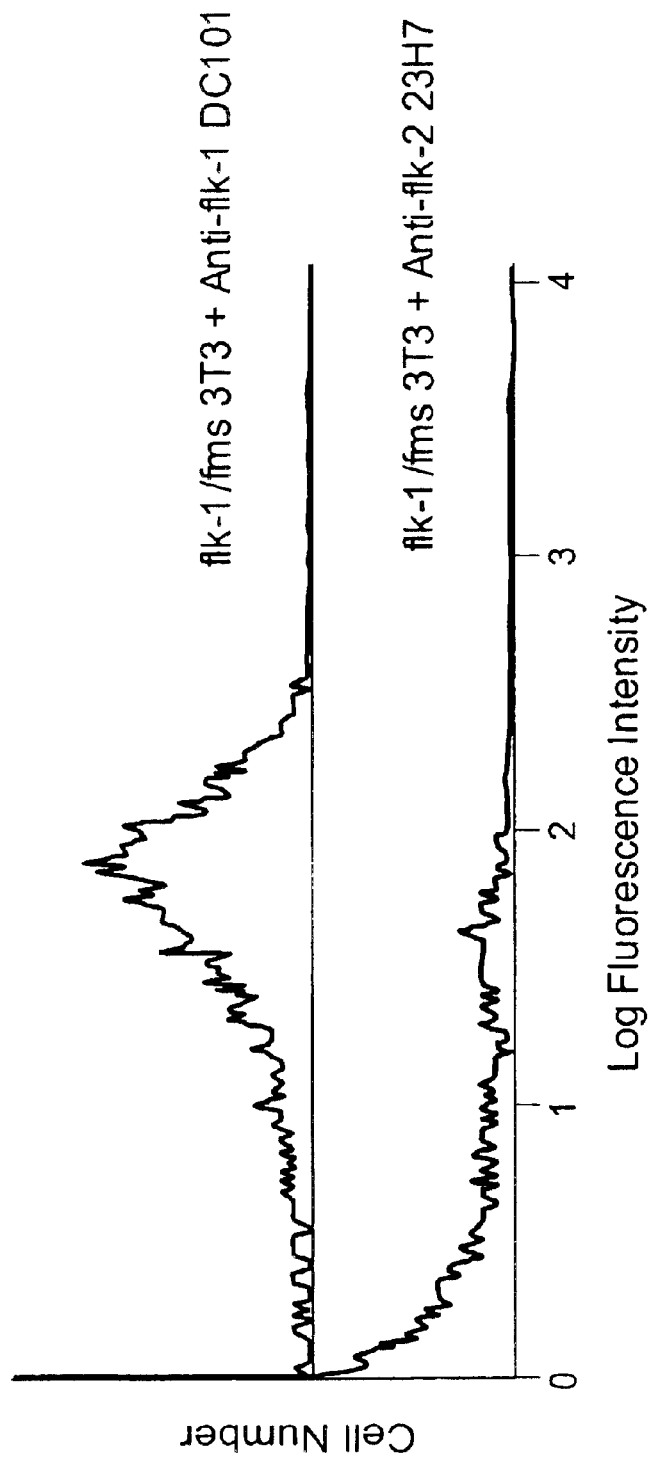
FIG. 6: FACS analysis of anti-FLK-1 mAb binding to FLK-1/fms transfected 3T3 Cells (C441). Transfected FLK-1/fms 3T3 cells were incubated on ice for 60 minutes with 10 µg/ml of the anti-FLK-1 MAb DC-101 or the isotype matched irrelevant anti-FLK-1 MAb 23H7. Cells were washed and reincubated with 5 µg of goat anti-mouse IgG conjugated to FITC, washed, and analyzed by flow cytometry to determine antibody binding. Data shows the level of fluorescence for DC-101 to C441 cells relative to that detected with the irrelevant MAb 23H7.
Figure 7:
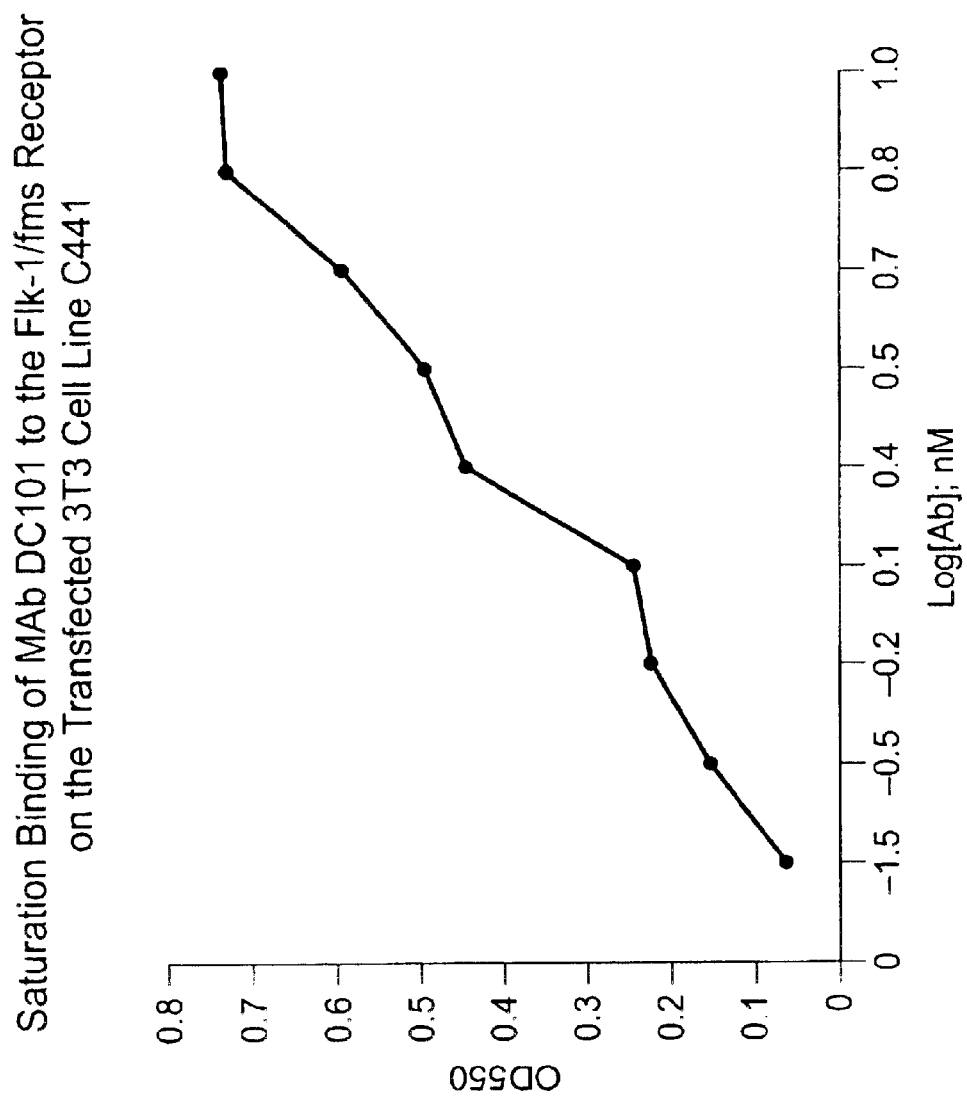
FIG. 7: Saturation binding of mAb DC-101 to the FLK-1/fms receptor on the transfected 3T3 cell line C441. Confluent C441 cells were incubated in 24 well plates with increasing concentrations of MAb DC-101 (50 ng/ml to 2 µg/ml) for two hours at 4° C. Cells were washed and incubated with 5 µg anti-rat IgG-biotin conjugate. To detect binding, cells were washed, incubated with a 1:1000 dilution of streptavidin-HRP, washed and incubated in a colormetric detection system (TMB). Data represents the absorbance at 540 nm versus increasing concentrations of MAb DC-101. The binding of the secondary antibody to cells alone was subtracted from each determination to adjust for non-specific binding. Data represents the average of three independent experiments.

The mAb was assayed by FACS analysis for binding to 3T3 cells transfected with the FLK-1/fms receptor (C441 cells). The results, shown in FIG. 6, demonstrate that the chimeric FLK-1/fms expressed on the surface of C441 cells is specifically recognized by mAb DC-101 and not by an antibody of the same isotype raised against the related tyrosine kinase receptor, FLK-2. The efficacy of the mAb-receptor interaction at the cell surface was determined from assays in which varying levels of mAb binding was measured on intact C441 cells. These results, shown in FIG. 7, indicate that mAb binds to the FLK-1/fms receptor with a relative apparent affinity of approximately 500 ng/ml. These results indicate that the mAb has a strong affinity for cell surface expressed FLK-1.

Example V-5
Reactivity of DC-101 by Immunoprecipitation

Figure 8:
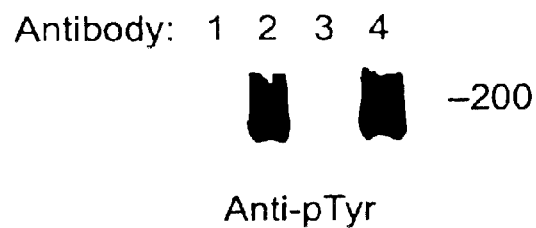
FIG. 8: Immunoprecipitation of phosphorylated FLK-1/fms from VEGF stimulated FLK-1/fms transfected 3T3 cells. Cells were stimulated with VEGF as described in the Experimental Procedures and lysates were immunoprecipitated with irrelevant or relevant antibodies as follows: 1. rat anti-FLK2 IgG2a (Mab 2A13); 2. rat anti-FLK-1 IgG1 (Mab DC-101); 3. rat anti-FLK2 IgG1 (Mab 23H7); 4. rabbit anti-fms polyclonal antibody. Immunoprecipitated protein was subjected to SDS PAGE followed by Western blotting. The immunoprecipitation of VEGF activated receptor was detected by probing the blots with an anti-phosphotyrosine antibody.
Figure 9:
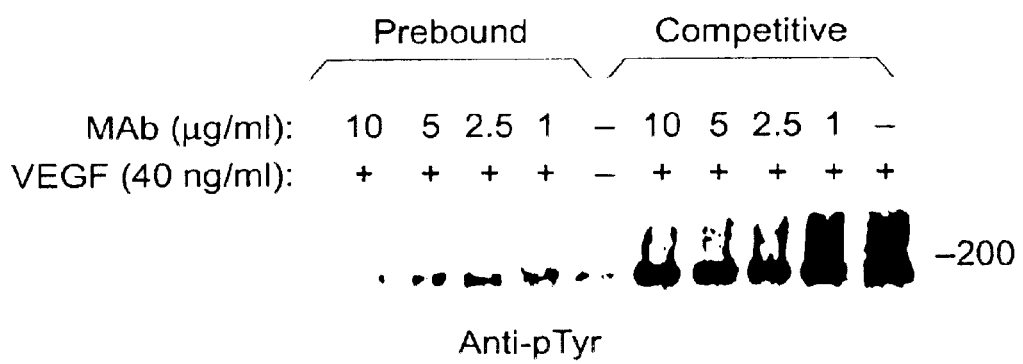
FIG. 9: Sensitivity of VEGF-induced phosphorylation of the FLK-1/fms receptor to inhibition by mAb DC-101. Prebound and competitive assays were performed with 40 ng/ml of VEGF at the antibody concentrations indicated. Cell lysates were prepared for receptor detection with anti-phophotyrosine as described in the Examples below.

The extent of DC-101 reactivity with the FLK-1/fms receptor was further assessed by determining the capacity of the antibody to immunoprecipitate the receptor following activation by VEGF. FIG. 8 shows an immunoprecipitation by mAb DC-101 of the phosphorylated FLK-1/fms receptor from VEGF stimulated C441 cells. The results show that the DC-101 monoclonal and anti-fms polyclonal antibodies display similar levels of receptor interaction while rat anti FLK-2 antibodies 2H37 (IgG1) and 2A13 (IgG2a) show no reactivity. Experiments were then performed to determine whether mAb DC-101 could neutralize the VEGF induced phosphorylation of FLK-1/fms at maximal stimulatory concentrations of ligand (40 ng/ml). In these studies, monoclonal antibody was added to monolayers either simultaneously with ligand or prior to ligand stimulation and assayed for 15 minutes at room temperature. These conditions were studied to determine both the competitive effects (competitive inhibition) of the antibody on receptor/ligand binding as well as the efficacy of prebound antibody to prevent receptor activation. The results of these assays, shown in FIG. 4, indicate that phosphorylation of the FLK-1/fms is reduced by the simultaneous addition of mAb with VEGF and markedly inhibited by antibody prebound to the receptor. A densitometry scan of these data revealed that mAb DC-101 interacts with FLK-1/fms to inhibit phosphorylation to a level that is 6% (lane 5, P) and 40% (lane 6, C) of the fully stimulated receptor control (lane 4). From these data we infer that mAb DC-101 strongly competes with the ligand-receptor interaction to neutralize FLK-1 receptor activation. To determine the sensitivity of the VEGF-FLK-1 interaction to inhibition by mAb DC-101, C441 cells were assayed with maximal VEGF levels in the presence of increasing concentrations of antibody. Assays were performed with the mAb under competitive and prebinding conditions. The results of these mAb titrations are shown in FIG. 9. A marked decrease in the phosphorylation of FLK-1 is observed when mAb DC-101 competes with VEGF antibody at concentrations greater than 0.5 µg/ml. These data also show that relatively low concentrations of prebound antibody (<1 µg/ml) are sufficient to completely inhibit receptor activation by ligand.

Example V-6
Activity of DC-101 by Phosphorylation Assay

Figure 10:
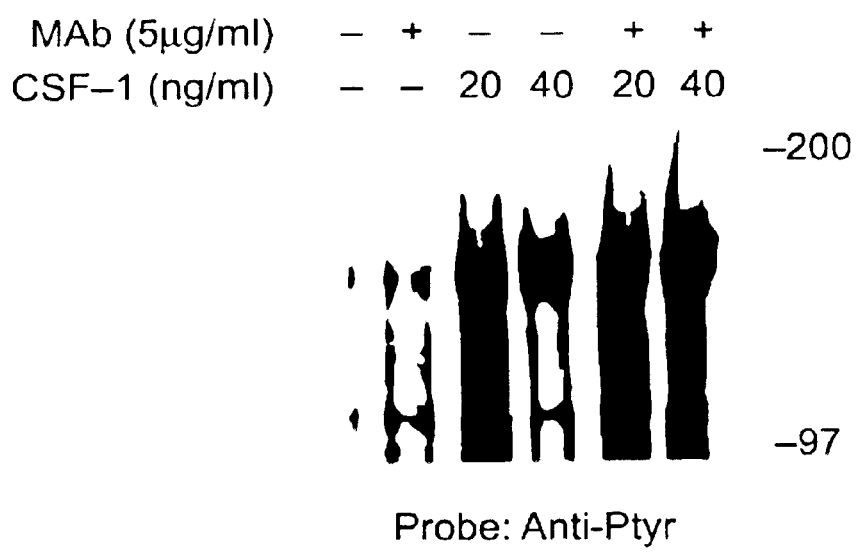
FIG. 10: Effect of mAb DC-101 on CSF-1 induced phosphorylation of the fms receptor. In (B), the fms/FLK-2 transfected 3T3 cell line, 10A2, was stimulated with optimal stimulatory levels of CSF-1 in the absence (Lanes 3 and 4) and presence (Lanes 5 and 6) of 5 µg/ml of MAb DC-101. Unstimulated cells assayed in the absence (Lane 1) or presence (Lane 2) of antibody serve as controls. Cell lysates were prepared for detection by anti-phosphotyrosine as described in the Examples below.

To further evaluate the antagonistic behavior of mAb DC-101 on receptor activation, phosphorylation assays were performed in which a fixed amount of antibody (5 µg/ml) was added to C441 cells stimulated with increasing amounts of ligand (FIG. 3a). The level of phosphorylation induced by each ligand concentration in the presence and absence of mAb DC-101 was also quantitated by densitometry readings. The plot of these data given in FIG. 3b indicates that the antibody was able to partially neutralize receptor phosphorylation even in the presence of excess amounts of VEGF. To evaluate the specificity of mAb DC-101 on receptor activation, the antibody was tested for its ability to competitively inhibit CSF-1 induced activation of the fms/FLK-2 receptor in the 3T3 transfected cell line, 10A2. In these experiments 5 µg/ml of mAb DC-101 was tested together with CSF-1 concentrations (20–40 ng/ml) that are known to result in full activation of the receptor. These results, which are shown in FIG. 10, indicate that mAb DC-101 has no effect on the CSF-1 mediated phosphorylation of the fms/FLK-2 receptor.

Example V-7
DC-101 Inhibition by Pre-Incubation Studies

Figure 11:
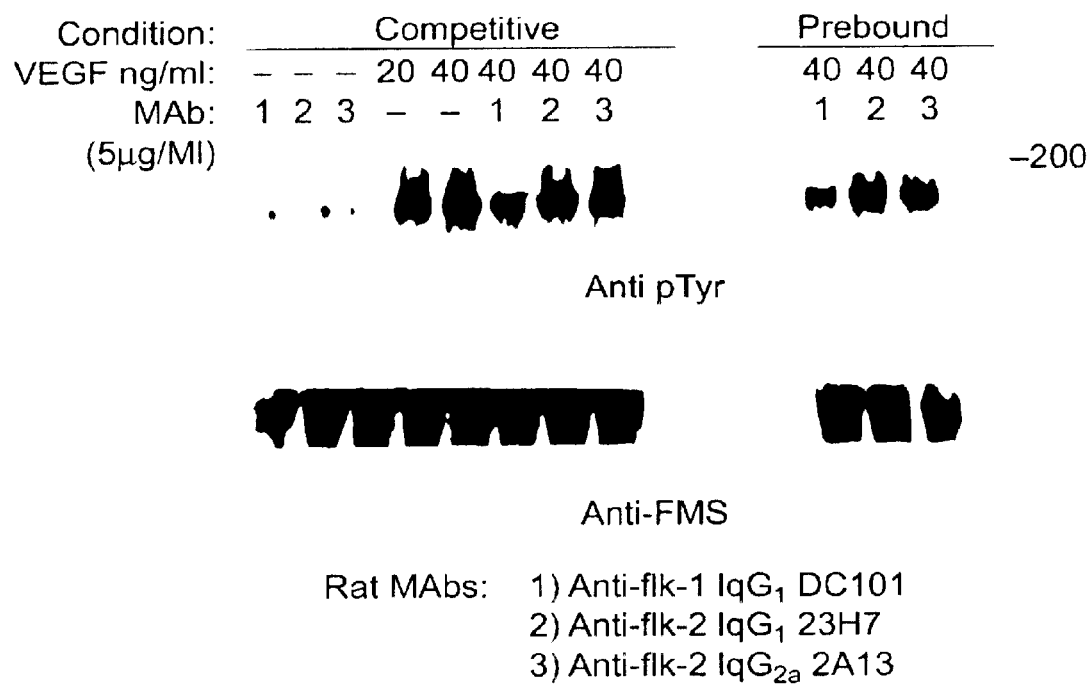
FIG. 11: Specificity of mAb DC-101 neutralization of the activated FLK-1/fms receptor. C441 cells were stimulated with 20 or 40 ng/ml of VEGF in the presence of DC-101 (IgG1) or the irrelevant anti-FLK-2 rat monoclonal antibodies 2A13 (IgG2a) or 23H7 (IgG1). Assays were performed with each antibody in the absence of VEGF (Lanes 1 to 3) and in the presence of VEGF under competitive (lanes 4 to 8) or prebound (lanes 9 to 11) conditions. Cell lysates were prepared for detection by anti-phosphotyrosine as described in the Examples below. Blots were stripped and reprobed to detect the FLK-1/fms receptor using a rabbit polyclonal antibody to the C-terminal region of the fms receptor.

The extent and specificity of antibody inhibition was further assessed by studies in which DC-101 or an irrelevant antibodies were preincubated with cells before the addition of ligand to assure maximal interaction of antibody with receptor. In these experiments, monolayers were preincubated with either 5 µg/ml of DC-101, a rat anti-FLK-2 mAb (2A13) or a control rat IgG1 (Zymed Labs) prior to the addition of 40 ng/ml of VEGF. For comparison, competitive assays were run in which antibodies and VEGF were added simultaneously. The results of these studies show that only the preincubation of the anti-FLK-1 monoclonal antibody with FLK-1/fms transfected cells completely abrogates receptor activation by VEGF while phosphorylation of FLK-1 by VEGF is not affected by the addition of irrelevant isotype matched rat antibodies. The reactivity of the same blot probed with the anti-fms polyclonal (FIG. 11) shows an equal level of receptor protein per lane. These data indicate that the lack of phosphorylation observed with mAb DC-101 treated cells was due to the blockage of a VEGF-induced phosphorylation of equal amounts of expressed receptor.

Example V-8
Interaction of Antibodies with Homologous Receptor Forms

Figure 12:
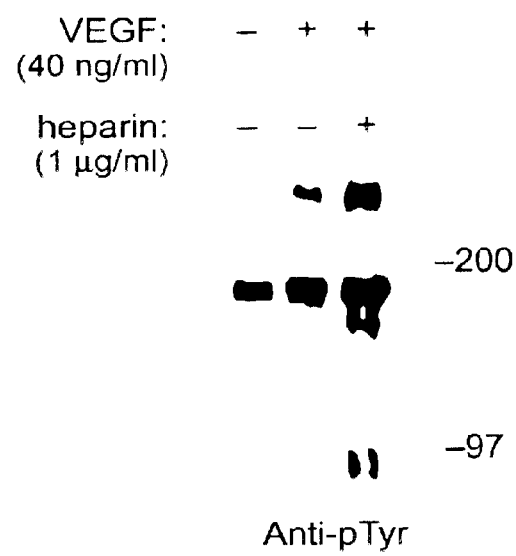
FIG. 12: Immunoprecipitation of phosphorylated receptor bands from VEGF stimulated HUVEC cells. HUVEC cells were grown to subconfluency in endothelial growth medium (EGM) for three days without a change of medium. Receptor forms were immunoprecipated by MAb DC-101 from lysates of unstimulated cells (Lane 1), VEGF stimulated cells (lane 2), and cells stimulated with VEGF in the presence of 1 µg/ml heparin (Lane 3). Phosphorylation assays, immunoprecipitations, and detection of the phosphorylated receptor forms were performed as described in the Experimental Procedures.
Figure 13:
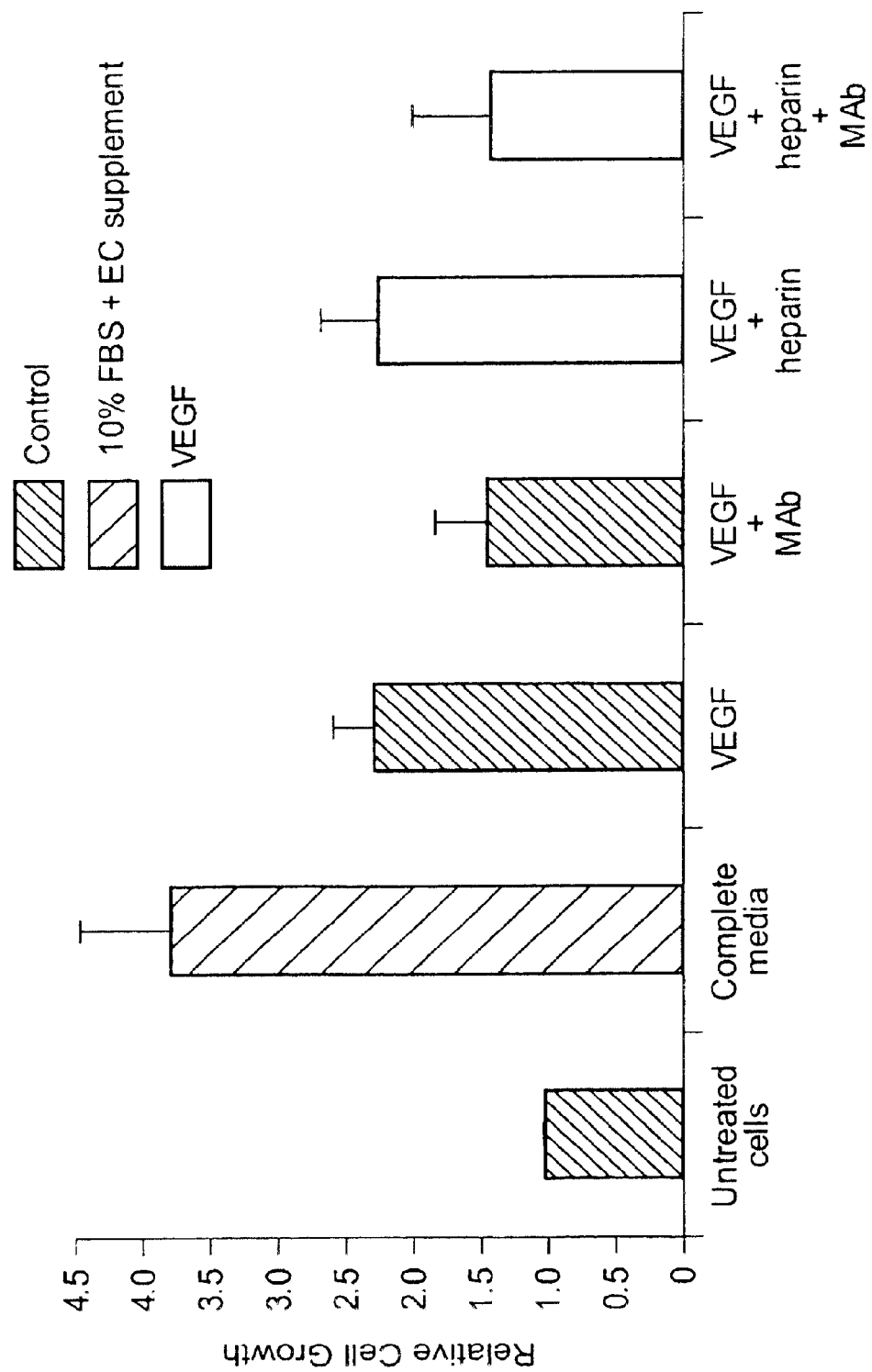
FIG. 13: Effect of mAb DC-101 on the proliferation of HUVEC cells in response to VEGF. Cells were grown for 48 hours as described in the legend to FIG. 6. Cells were then subjected to the following assay conditions: no addition to medium (untreated); a change of fresh endothelial growth medium (complete medium); the addition of 10 ng/ml of VEGF in the absence or presence of 1 µg/ml heparin; and VEGF and VEGF-heparin treated cells assayed in the presence of 1 µg/ml of DC-101. Cells were assayed for proliferation by colormetric detection at 550 nm using a cell proliferation assay kit (Promega).

Experiments were then conducted to determine whether the anti-FLK-1 monoclonal antibodies interact with homologous receptor forms on human endothelial cells. A titration of increasing concentrations of DC-101 on cloned HUVEC cells (ATCC) indicated that the antibody displayed a complex binding behavior. The data represent differential antibody interactions with VEGF receptors reported to occur on endothelial cells (Vaisman et al., J. Biol. Chem. 265, 19461–19466, 1990). The specificity of DC-101 interaction with VEGF stimulated HUVEC cells was then addressed using phosphorylation assays under similar conditions as those reported for FIG. 8. In these studies DC-101 immunoprecipitates protein bands from HUVEC cells that have molecular weights similar to those reported for cross linked VEGF-receptor bands when the ligand component is subtracted (FIG. 12). These bands display an increased phosphorylation when cells are stimulated by VEGF (compare lanes 1 and 2 in FIG. 12). In addition, the VEGF induced phosphorylation of the receptor bands is potentiated by the inclusion of 1 μg/ml heparin in the assay (lane 3 in FIG. 12). These findings are consistent with previous reports of increased VEGF binding to endothelial cells in the presence of low concentrations of heparin (Gitay-Goren et al., J. Biol. Chem. 267, 6093–6098.1992).

It is difficult to ascertain which immunoprecipitated protein interacts with DC-101 to generate the complex of phosphorylated bands observed in FIG. 12 given the various receptor forms shown to bind VEGF on HUVEC and the possibility of their association upon stimulation. Cell surface expressed receptor forms with molecular weights of approximately 180 (KDR), 155, 130–135, 120–125 and 85 have been reported to bind VEGF on HUVEC. Such findings address the possibility that several different receptor forms may heterodimerize upon ligand stimulation in a manner similar to that reported for KDR-FLT-1. However, with the exception of KDR, the exact nature and role of these receptor forms have yet to be defined. Consequently, antibody reactivity may result from interaction(s) with one of several VEGF receptors independent of KDR.

DC-101 does not react with human KDR in an ELISA format nor bind to freshly isolated HUVEC by FACS analysis. These results suggest that a direct interaction of DC-101 with human KDR is highly unlikely.

Unlike DC-101, Mab 25 and Mab 73 both react with human KDR in an ELISA format and bind to freshly isolated HUVEC by FACS analysis.

Example V-9
Mitogenic Assays of HUVEC

An inhibitory effect of DC-101 on endothelial cells was observed when the antibody was tested in mitogenic assays of HUVEC cells (ATCC) stimulated with VEGF in the presence and absence of antibody (FIG. 12). These results show that a marked increase in cell proliferation by VEGF is reduced approximately 35% by DC-101. Heparin shows no differential effect on cell growth under the growth conditions employed in these assays.

Since DC-101 can exert effects on VEGF induced proliferation and receptor phosphorylation of HUVEC it is conceivable that these results are due to a Mab interaction with an undefined receptor form which is poorly accessible at the cell surface, but which plays some role, albeit minor, in HUVEC growth. Also, the immunoprecipitation of phosphorylated bands of the correct molecular weight by DC-101 from VEGF stimulated HUVEC also supports the notion that DC-101 may interact with an undefined FLK-1 like protein that associates with an activated receptor complex.

Example V-10
Binding of Mab 25 and Mab 73 to C441 Cells and HUVEC

Mabs 25 and 73 bind to C44 1 and HUVEC by FACS analysis and show internalization in both cell lines. Results from western blots show that both anti-FLK-1 Mabs can detect the band(s) for the FLK/fns receptor in immunoprecipitates by an anti-fms polyclonal antibody from C441 cells. (See example IV-2 above for protocol.) These antibodies elicit a specific neutralization of VEGF induced activation of the FLK-1fms receptor and have no effect on the phosphorylation of the mouse PDGF receptor by PDGF or the human EGF receptor by EGF. (See example IV-1 above for protocol.) They have the capacity to inhibit VEGF stimulated HUVEC in proliferation assays to 50% whereas DC-101 affects growth to a far lesser extent.

Example V-11
Immunoprecipitation of KDR with Mab25 and Mab73

KDR represents one of the phosphoproteins immunoprecipitated by the Mab25 and Mab 73 from activated HUVEC. KDR was detected in western blot and immunoprecipitation analyses using an anti-FLK-1/KDR polyclonal antibody (IM142) from VEGF-stimulated early passage HUVEC. Conversely, bands immunoprecipitated by these antibodies from VEGF-stimulated HUVEC are cross reactive with IM142 but not an anti-FLT-1 polyclonal antibody. These findings infer that the Mabs may affect the activity of KDR in HUVEC based on experimental evidence implicating KDR as the VEGF receptor responsible for the proliferative response in activated endothelial cells. (See example IV-3 above for protocol.)

Example VI
Presence of VEGF Receptor Forms on Non-Endothelial (Tumor) Cells

Several tumor lines were screened for protein reactivity with DC-101 by immunoprecipitation and detection with antiphosphotyrosine. Immunoblots from the cell lines 8161 (melanoma) and A431 (epidermoid carcinoma) yielded phosphorylated bands with molecular weights of approximately 170 and 120 kD. These results indicate that a human VEGF receptor form is expressed in non-endothelial cells, such as tumor cells.

Similar experiments have shown that a KDR like receptor is expressed in an ovarian carcinoma cell line, OVCAR-3. These cells also appear to secrete VEGF. Phosphorylated bands are immunoprecipitated by an anti-KDR polyclonal antibody from VEGF-stimulated OVCAR-3 cells that are reactive with anti-FLK-1 Mabs by western blotting. Also, bands immunoprecipitated by the murine Mabs from these cells show cross reactivity with the same polyclonal antibody. Furthermore certain murine anti-FLK-1 Mabs elicit an inhibitory effect on these cells in proliferation assays. These results demonstrate nonendothelial expression (i.e. on tumor cells) of human VEGF receptor forms. The data from the phosphorylation and proliferation assays also suggest that VEGF can modulate receptor activity in an autocrine and paracrine manner during tumorigenesis. (See Example IV-3 above for protocol.)

Example VII
In vivo Studies Using DC-101

Example VII-1
Inhibition in vivo of Angiogenesis by DC-101

Figure 5:
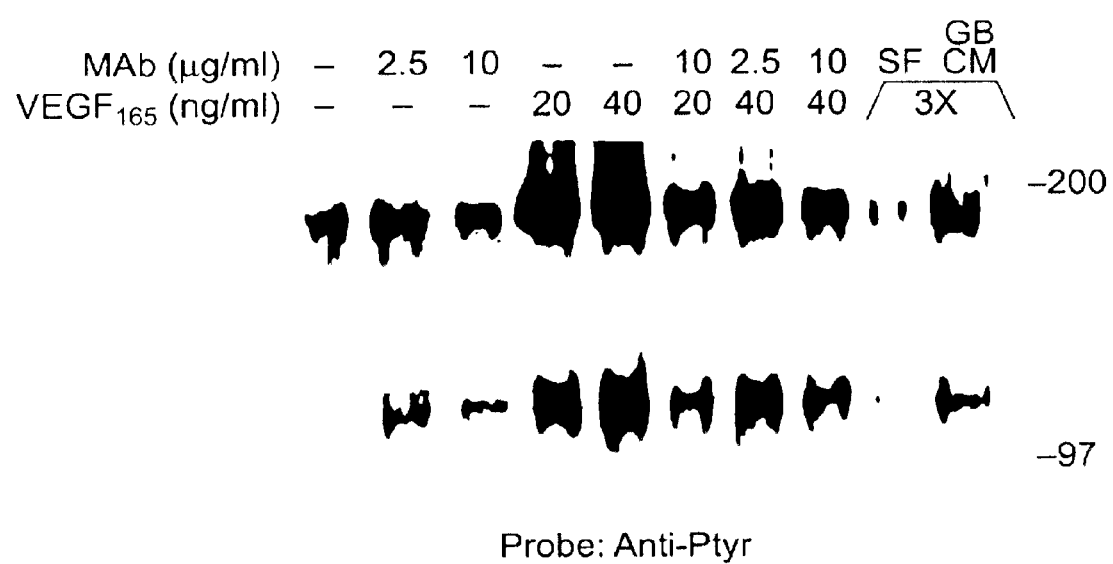
FIG. 5: VEGF-induced phosphorylation of the FLK-1/fms receptor by treatments with varying concentrations of monoclonal antibody DC-101 and conditioned media from glioblastoma cells (GB CM).

In vivo studies were designed to determine if an anti-FLK-1 monoclonal antibody would block the growth of VEGF-expressing tumor cells. In these experiments, a human glioblastoma multiform cell line was used that has high levels of VEGF message and secretes about 5 ng/ml of VEGF growth factor after a 24 hour conditioning in serum free medium (FIG. 5).

On day zero, athymic nude mice (nu/nu; Charles River Labs) were injected in the flank with 1–2 million glioblastoma cells. Beginning on the same day, animals received intraperitoneal injections of either DC-101 and control antibodies (100 µg/animal). The mice received subsequent antibody treatments on days 3, 5, 7, 10, 12, 14, 17, 19, and 21. Animals received injections of 100 µg of either DC-101 or a control rat antibody to the murine FLK-2 (2A13) receptor on days 0, 3, 5, 7, 10, 12, 14, 17, 19, and 21 for a total inoculation of 1 mg/animal. Tumors began to appear by day 5 and followed for 50 days. Tumor size was measured daily with a caliper and tumor volume calculated by the following formula: p/6×larger diameter×(smaller diameter)$^2$ (Baselga J. Natl. Cancer Inst. 85: 1327–1333). Measurements were taken at least three times per week and tumor volume calculated as described above. One tumor bearing animal in the DC-101 group died early in the study and was not used to determine statistical significance between the groups.

Figure 14A:
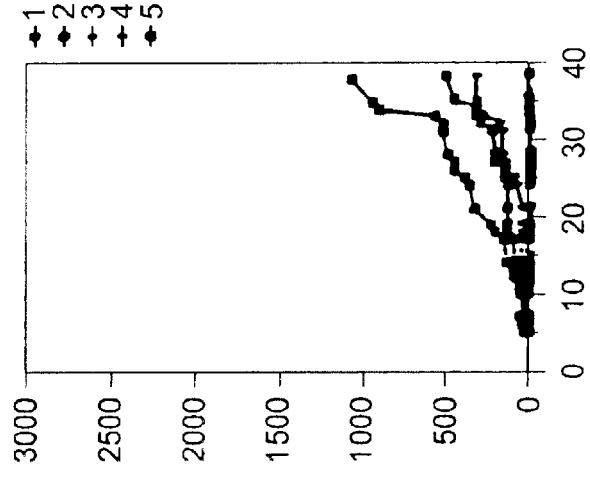
FIGS. 14a and 14b FIG. 14a: Reduction in tumor growth of individual animals with DC-101 (rat anti-flk-1 monoclonal antibody).
Figure 14B:
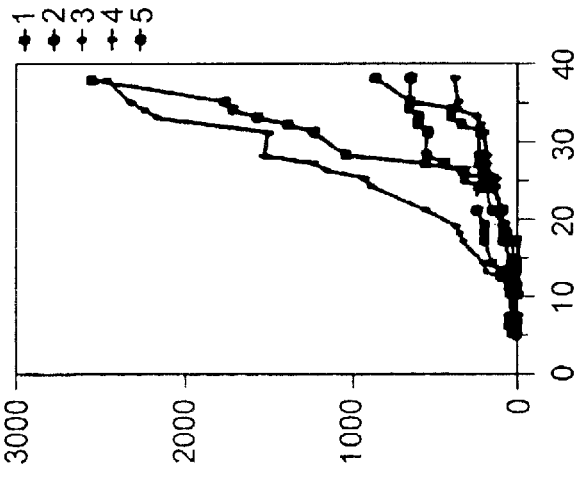

FIGS. 14a and 14b show a comparison between the DC-101 and the control 2A13 group of reduction in tumor growth over 38 days in individual animals. Although all animals developed tumors of varying sizes and number during the course of the study, DC-101-treated mice showed an overall delay in tumor progression. One mouse in the DC-101 group remained tumor free until day 49 when a small growth was observed. Even then, tumor growth was markedly suppressed. Statistical analysis of the data was done to assess differences in tumor size between the two groups. Data was subjected to a standard analysis of covariance where tumor size was regressed on time with treatment as a covariate. The results showed that reduction in tumor size over time for the DC-101 group was significantly different ($p<0.0001$) from that seen for 2A13 injected mice.

Figure 15:
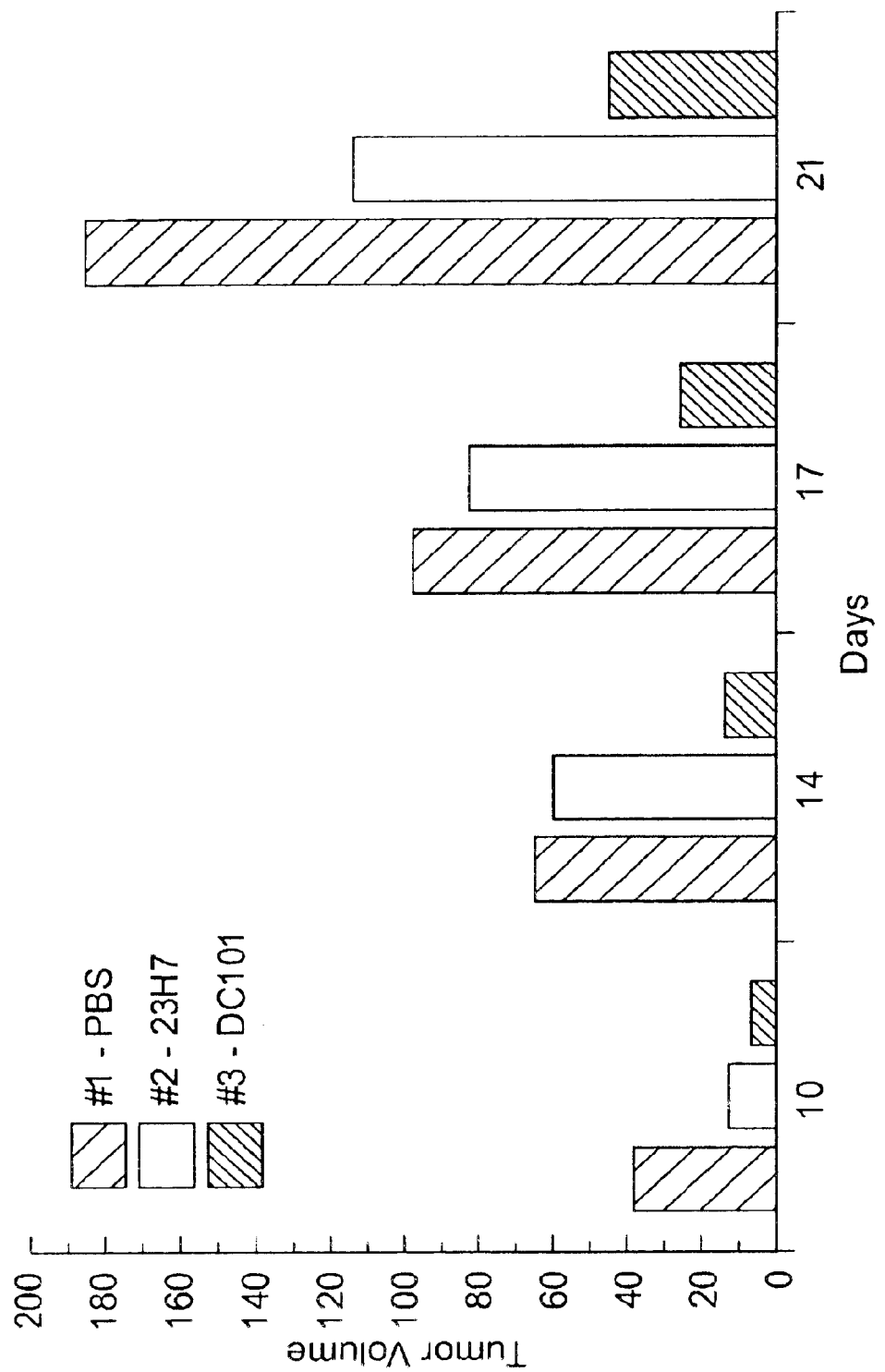
FIG. 15: Athymic nude mice were injected subcutaneously with human glioblastoma cell line GBM-18 and divided into three groups: a PBS control, an irrelevant rat IgG1 control 23 H7, and DC-101. Treatments were administered simultaneously with tumor xenografts and continued for four weeks.

FIG. 15 shows the therapeutic efficacy of DC-101 in athymic nude mice transplanted with the human glioblastoma tumor cell line GBM-18, which secretes VEGF. Nude mice were injected subcutaneously with GBM-18 cells and divided into three groups of treatment: a PBS control, an irrelevant rat IgG1 control, and DC-101. Treatments were administered simultaneously with tumor xenografts and continued for four weeks. The results showed that GBM-18 tumor growth in DC-101-treated nude mice was significantly reduced relative to controls. This experiment indicates that DC-101 suppresses tumor growth by blocking VEGF activation of FLK-1 on tumor associated vascular endothelial cells, and that DC-101 has therapeutic value as an anti-angiogenic reagent against vascularized tumors secreting VEGF.

Monoclonal antibodies to FLK-1 receptor tyrosine kinase inhibit tumor invasion by abrogating angiogenesis. Invasive growth and angiogenesis are essential characteristics of malignant tumors. Both phenomena proved to be suitable to discriminate benign from malignant keratinocytes in a surface transplantation assay. After transplantation of a cell monolayer attached to a collagen gel onto the back muscle of nude mice, all tumor cells initially formed organized squamous epithelia, but only malignant keratinocytes grew invasively within 2–3 weeks. Both benign and malignant cells induced angiogenesis. Angiogenic response to malignant cells, however, occurred earlier, is much stronger, and capillary growth directed toward malignant epithelia. Moreover, in transplants of benign tumor cells, capillaries regressed after 2–3 weeks, whereas malignant keratinocytes maintain the level of ongoing angiogenesis. The vascular endothelial growth factor (VEGF) and its cognate receptor play a pivotal role in tumor angiogenesis. The administration of DC-101 disrupted ongoing angiogenesis leading to inhibition of tumor invasion. The antibody prevented maturation and further expansion of newly formed vascular network, but did not significantly interfere with initial angiogenesis induction. These results provide evidence that tumor invasion requires precedent angiogenesis, and that the VEGF receptors are crucial in maintaining angiogenesis in this model system.

Example VII-2
Effect of Different Concentrations of DC-101 on Established Glioblastoma (gbm-18) Tumors Athymic mice (nu/nu) were inoculated subcutaneously with GBM-18 (human glioblastoma multiformae). Antibody therapy was initiated when the tumors reached an average volume of 100–200 mm$^3$. Treatment consisted of six injections (twice weekly for 3 weeks) of the following: (i) DC-101 at 200, 400 or 800 µg/injection; (ii) an irrelevant isotype matched rat IgG (400 µg/injection); or, (iii) PBS. Tumor volumes were measured with a caliper. Tumor inhibition in the DC-101 groups was found to be significant (*) vs. the PBS and irrelevant monoclonal antibody groups.

Another experiment demonstrates the effects of the rat anti-FLK-1 monoclonal antibody DC-101 on the growth of GBM-18 tumors in nude mice. Animals (nu/nu; Charles River Labs; ten animals per group) were injected subcutaneously with GBM-18 cells (human glioblastoma [100]; 1 million per animal) on day 0. Treatments with PBS or DC-101(200 µg per injection) were begun on day 7 and continued twice weekly for 3 weeks (6×). Graphs show a plot of the mean tumor volumes and regressed data for each group over time with their respective tumor growth rates (slopes given as λ; solid lines) and 99% confidence limits (dotted lines). The slope of the line for animals treated with DC-101 was significantly different from that of PBS ($p \leq 0.01$). It is important to note that an irrelevant rat IgG1 monoclonal antibody (anti-mouse IgA; Pharmigen) had no effect on the growth of GBM-18 xenografts and gave results similar to that observed with PBS (data not shown).

Example VIII
Anti-FLK-1 Antibody Selectively Increases Radiation-Induced Cure Rate of Human Tumor Xenografts in Nude Mice This example evaluates whether the monoclonal antibody DC-101 blocking the crucial VEGF receptor-2, FLK-1, on murine endothelial cells of tumor vessels increases curability of tumor xenografts by fractionated radiotherapy (RT), and whether the antibody concurrently modulates the radiation reaction of normal tissue (mouse skin).

Materials & Methods: The human small cell lung carcinoma 54A and glioblastoma multiforme U87 were implanted subcutaneously into the hind leg of nude mice. Treatment was begun when a tumor reached 8 mm in diameter (day 0). DC-101 was injected intraperitoneally every 3 days at a dose of 20 or 40 mg/kg body-weight, for a total of 6 injections. Graded total doses of radiation were given in equal daily fractions on 5 consecutive days. On day 0, a mouse received the first injection of the antibody, or RT was started. For the combined treatment, DC-101 administration was commenced on day 0, and RT was begun on day 1. Tumor size was measured 2–3 times a week after treatment. The mice with locally controlled tumors were followed-up for 90 days after the last tumor recurrence was observed in any group. Acute reaction of skin in the field of tumor irradiation was evaluated using a scoring scale during the first 30 days after the beginning of RT.

Results: The antibody used alone induced growth inhibition (but not regression) of both tumors in a dose-dependent manner. The effect was more pronounced in 54A than in U87 xenografts. In combination with the lowest doses of radiation (25–30 Gy total), DC-101 provided an additional tumor growth delay when compared with RT alone, in either model. The antibody, also in a dose-dependent fashion, augmented the curative effect of RT. For example, at its higher dose, DC-101 decreased the dose of radiation necessary to control 50% of tumors locally: 1.7 fold in 54A xenografts (from 67.6 Gy for RT alone to 39.1 Gy for the combined therapy), and 1.3 fold in U87 (from 97.8 to 74.8 Gy). It is also of particular importance that such effects of DC-101 were selective for tumors. That is, no parallel changes of skin radiation reaction by the antibody were detected. As assessed in additional experiments, the DC-101 -induced enhancement of the radiation response of tumors was not associated with their radiosensitization or changes in oxygenation, while correlated with a significant decrease of the tumor interstitial fluid pressure by the antibody.

Conclusion: The results collectively suggest that the blockage of VEGF-signaling pathways by an antibody against the main receptor to these growth factor molecules can selectively potentiate the tumor curative response to fractionated RT; and thus, provide a therapeutic gain.

Example IX
Producing Single Chain Antibodies
Example IX-1(a)
Cell Lines and Proteins Primary-cultured HUVEC was maintained in EBM-2 medium at 37° C., 5% CO2. Cells were used between passage 2–5 for all assays. $VEGF_{165}$ protein was expressed in baculovirus and purified. Complementary DNA encoding the extracellular domain of KDR was isolated by RT-PCR from human fetal kidney mRNA and subcloned into the Bgl II and BspE I sites of the vector AP-Tag. In this plasmid the cDNA for KDR extracellular domain is fused in-frame with the cDNA for human placental AP. The plasmid was electroporated into NIH 3T3 cells together with the neomycin expression vector pSV-Neo and stable cell clones were selected with G418. The soluble fusion protein KDR-AP was purified from cell culture supernatant by affinity chromatography using immobilized monoclonal antibodies to AP.

Example IX-1(b)
Mice Immunization and Construction of Single Chain Antibody Phage Display Library Female BALB/C mice were given two intraperitoneal (i.p.) injections of 10 µg KDR-AP in 200 µl of RIBI Adjuvant System followed by one i.p. injection without RIBI adjuvant over a period of two months. The mice were also given a subcutaneous (s.c.) injection of 10 µg KDR-AP in 200 µl of RIBI at the time of the first immunization. The mice were boosted i.p. with 20 µg of KDR-AP three days before euthanasia. Spleens from donor mice were removed and the cells were isolated. RNA was extracted and mRNA was purified from total RNA of splenocytes. A scFv phage display library was constructed using the mRNA which was displayed on the surface of the filamentous phage M13.

In displaying the scFv on filamentous phage surface, antibody $V_H$ and $V_L$ domains are joined together by a 15 amino-acid-long linker $(GGGGS)^3$ and fused to the N-terminal of phage protein III. A 15 amino-acid-long E tag, which is followed by an amber codon (TAG), was inserted between the C-terminal Of $V_L$ and the protein III for detection and other analytic purposes. The amber codon positioned between the E tag and the protein III enables the construct to make scFv in surface-displaying format when transformed into a suppressor host (such as TGI cells) and scFv in soluble form when transformed into a nonsupressor host (such as HB2151 cells).

The assembled scFv DNA was ligated into the pCANTAB 5E vector. The transformed TG1 cells were plated onto 2YTAG plates and incubated. The colonies were scraped into 10 ml of 2YT medium, mixed with 5 ml 50% glycerol and stored at −70° C. as the library stock.

Example IX-1(c)
Biopanning

The library stock was grown to log phase, rescued with M13K07 helper phage and amplified overnight in 2YTAK medium (2YT containing 100 µ/ml of ampicillin and 50 µg/ml of kanamycin) at 30° C. The phage preparation was precipitated in 4% PEG/0.5M NaCl, resuspended in 3% fat-free milk/PBS containing 500 µg/ml of AP protein and incubated at 37° C. for 1 h to capture phage displaying anti-AP scFv and to block other nonspecific binding.

KDR-AP (10 µg/ml) coated Maxisorp Star tubes (Nunc, Denmark) were first blocked with 3% milk/PBS at 37° C. for 1 h, and then incubated with the phage preparation at room temperature for 1 h. The tubes were washed 10 times with PBST followed by 10 times with PBS (PBS containing 0.1% Tween 20). The bound phage was eluted at room temperature for 10 min. with 1 ml of a freshly prepared solution of 100 mM triethylamine. The eluted phage were incubated with 10 ml of mid-log phase TG1 cells at 37° C. for 30 min. stationary and 30 min. shaking. The infected TG1 cells were then plated onto 2YTAG plates and incubated overnight at 30° C.

Ninety-nine percent (185/186) of clones screened after the third round of panning were found to be specific KDR binders. However, only 15 (8%) of these binders could block KDR binding to immobilized VEGF. DNA BstN I fingerprinting of these 15 clones indicated the presence of 2 different digestion patterns; whereas 21 randomly picked VEGF nonblockers yielded 4 different patterns. All the digestion patterns were also seen in clones identified after the second round of panning. Representative clones of each digestion pattern were picked from clones recovered after the 2nd round of panning and subject to DNA sequencing. Out of 15 clones sequenced, 2 unique VEGF blockers and 3 nonblockers were identified. One scFv, p2A7, which neither binds to KDR nor blocks VEGF binding to KDR, was selected as a negative control for all studies.

Example IX-1 (d)
Phage ELISA

Individual TG1 clones were grown at 37° C. in 96 well plates and rescued with M13K07 helper phage as described above. The amplified phage preparation was blocked with ⅙ volume of 18% milk/PBS at RT for 1 h and added to Maxi-sorp 96-well microtiter plates (Nunc) coated with KDR-AP or AP (1 µg×100 1). After incubation at room temperature for 1 h, the plates were washed 3 times with PBST and incubated with a rabbit anti-M13 phage Ab-HRP conjugate. The plates were washed 5 times, TMB peroxidase substrate added, and the OD at 450 nm read using a microplate reader and scFv antibodies were identified and sequenced.

Example IX-1(e)
Preparation of Soluble scFv

Phage of individual clones were used to infect a nonsuppressor E. coli host HB2151 and the infectant selected on 2YTAG-N plates. Expression of scFv in HB2 151 cells was induced by culturing the cells in 2YTA medium containing 1 mM isopropyl-1-thio-B-D-galactopyranoside at 30° C. A periplasmic extract of the cells was prepared by resuspending the cell pellet in 25 mM Tris (pH 7.5) containing 20% (w/v) sucrose, 200 mM NaCl, 1 mM EDTA and 0.1 mM PMSF, followed by incubation at 4° C. with gentle shaking for 1 h. After centrifugation at 15,000 rpm for 15 min., the soluble scFv was purified from the supernatant by affinity chromatography using the RPAS Purification Module (Pharmacia Biotech).

Example IX-2
Assays

Example IX-2(a)
Quantitative KDR Binding Assay

Two assays were employed to examine quantitatively the binding of purified soluble scFv to KDR.

Four different clones, including the two VEGF blockers, p1C11 and p1F12, one nonblocker, the dominant clone p2A6 and the nonbinder p2A7, were expressed in shaker flasks using a nonsuppressor host E.coli HB2151 cells. The soluble scFv was purified from the periplasmic extracts of E. coli by anti-E-tag affinity chromatography. The yield of purified scFv of these clones ranged from 100 –400 μg/liter culture.

In the direct binding assay, various amounts of soluble scFv were added to KDR-coated 96-well Maxi-sorp microtiter plates and incubated at room temerature for 1 h, after which the plates were washed 3 times with PBST. The plates were then incubated at room temperature for 1 h with 100 μl of mouse anti-E tag antibody followed by incubation with 100 p1 of rabbit anti-mouse antibody-HRP conjugate. The plates were washed and developed following the procedure described above for the phage ELISA.

In another assay, i.e., the competitive VEGF blocking assay, various amounts of soluble scFv were mixed with a fixed amount of KDR-AP (50 ng) and incubated at room temperature for 1 h. The mixture were then transferred to 96-well microtiter plates coated with $VEGF_{165}$ (200 ng/well) and incubated at room temperature for an additional 2 h, after which the plates were washed 5 times and the substrate for AP was added to quantify the bound KDR-AP molecules. $IC_{50}$, i.e., the scFv concentration required for 50% inhibition of KDR binding to VEGF, was then calculated.

Figure 16:
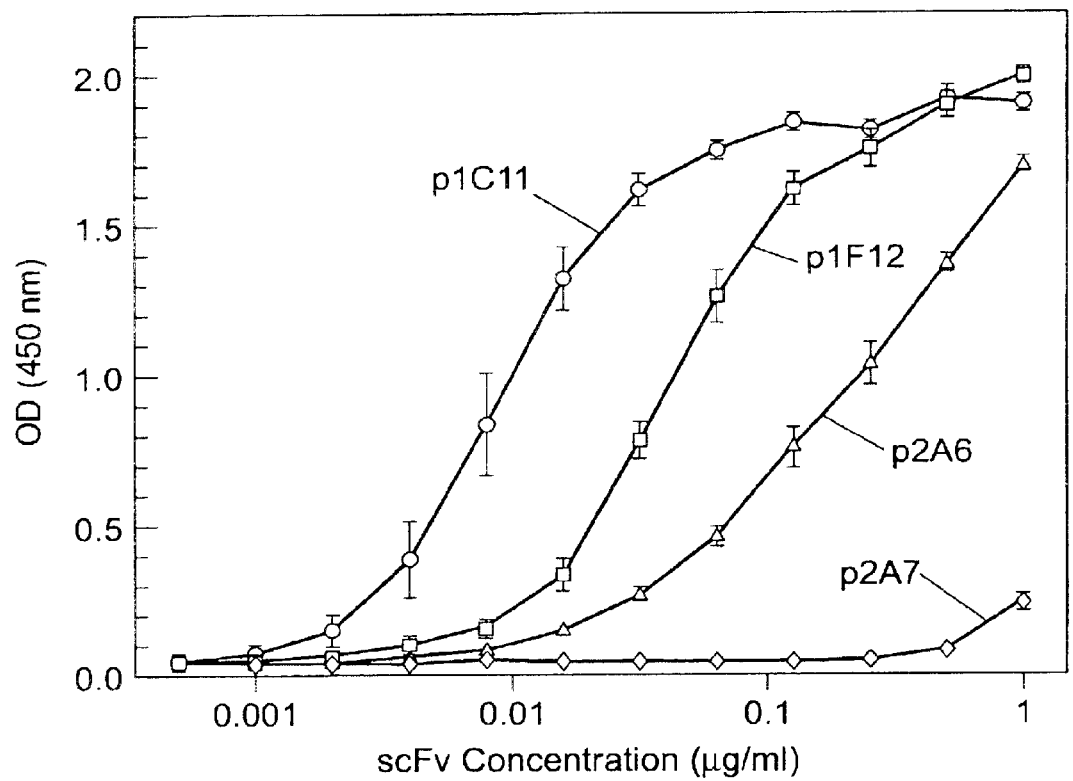
FIG. 16: A graph showing the direct binding of different scFv antibodies (p1C11, p1F12, p2A6 and p2A7) to immobilized KDR.
Figure 17:
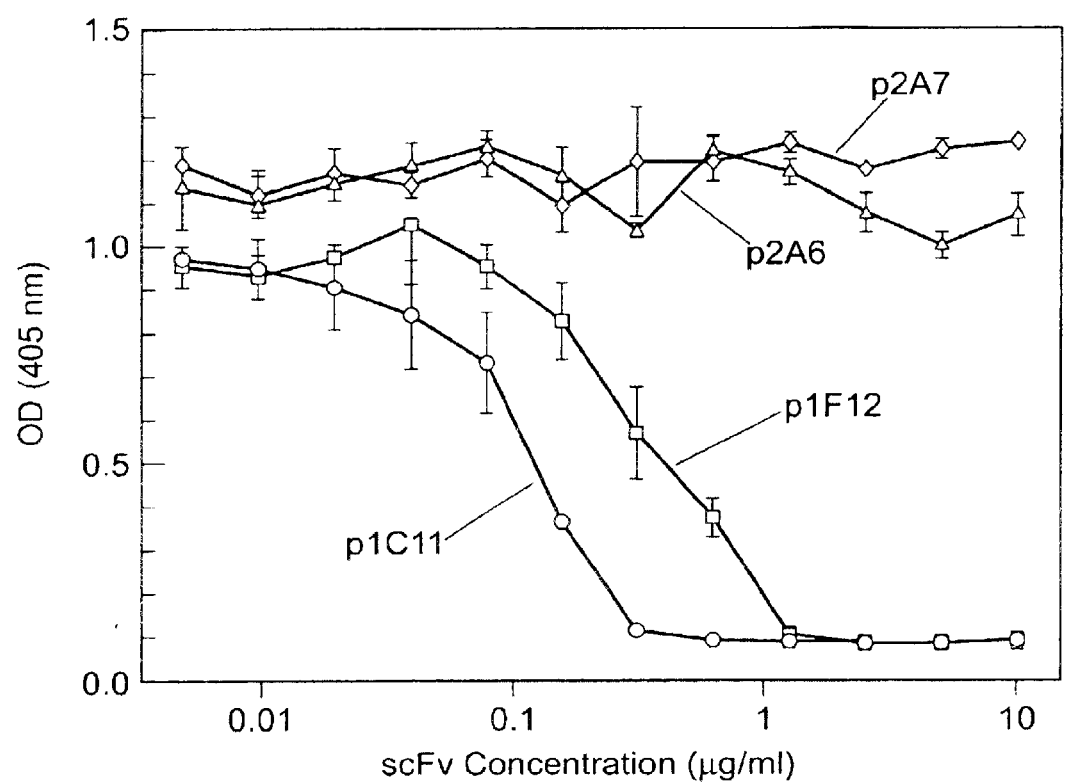
FIG. 17: A graph showing the inhibition of binding of KDR to immobilized $VEGF_{165}$ by different scFv antibodies (p1C11, p1F12, p2A6 and p2A7).

FIG. 16 shows the dose-dependent binding of scFv to immobilized KDR as assayed by a direct binding ELISA. Clone p1C11 and p1F12, but not p2A6, also block KDR binding to immobilized VEGF as shown in FIG. 17. Data shown in FIG. 17 are the means±SD of triplicate determinations. The negative control clone, p2A7, did not bind to KDR nor block KDR binding to VEGF (FIG. 16 and 17). Clone p1C 11, the dominant clone after each round of panning, showed the highest KDR binding capacity and the highest potency in blocking VEGF binding to KDR (Table 1). The antibody concentrations of clone p1C11 required for 50% of maximum binding to KDR (FIG. 16) and for 50% of inhibition of KDR binding to VEGF (FIG. 17) were 0.3 nM and 3 nM, respectively (See Table 1). FACS analysis demonstrated that p1C11, p1F12 and p2A6 were also able to bind to cell surface expressed receptor on HUVEC.

Example IX-2(b)
BIAcore Analysis of the Soluble scFv

The binding kinetics of soluble scFv to KDR were measured using BIAcore biosensor (Pharmacia Biosensor). KDR-AP fusion protein was immobilized onto a sensor chip and soluble scFv were injected at concentrations ranging from 62.5 nM to 1000 nM. Sensorgrams were obtained at each concentration and were evaluated using a program, BIA Evaluation 2.0, to determine the rate constant kon and koff. Kd was calculated from the ratio of rate constants koff/kon.

Table 1 shows the results of the surface plasmon resonance on a BIAcore instrument. The VEGF-blocking scFv, p1C11 and p1F12, bound to immobilized KDR with Kd of 2.1 and 5.9 nM, respectively. The non-blocking scFv, p2A6, bound to KDR with approximately a 6-fold weaker affinity (Kd, 11.2 nM) than the best binder p1C11, mainly due to a much faster dissociation rate. As anticipated, p2A7 did not bind to the immobilized KDR on the BIAcore.

Example IX-2(c)
Phosphorylation Assay

Phosphorylation assays were performed with early passage HUVEC following a protocol described previously. Briefly, HUVEC were incubated in serum free EBM-2 base medium supplemented with 0.5% bovine serum albumin at room temperature for 10 min. in the presence or absence of scFv antibodies at 5 μg/ml, followed by stimulation with 20 ng/ml $VEGF_{165}$ at room temperature for an additional 15 min. The cells were lysed and the KDR receptor was immunoprecipitated from the cell lysates with Protein A Sepharose beads coupled to a rabbit anti-KDR polyclonal antibody (ImClone Systems Incorporated). The beads were washed, mixed with SDS loading buffer, and the supernatant subjected to Western blot analysis. To detect KDR phosphorylation, blots were probed with an anti-phosphotyrosine Mab, 4G10. For the MAP kinase activity assay, cell lysates were resolved with SDS-PAGE followed by Western blot analysis using a phospho-specific MAP kinase antibody. All signals were detected using ECL.

Results showed that VEGF-blocking scFv p1C11, but not the non-blocking scFv p2A6, was able to inhibit KDR receptor phosphorylation stimulated by VEGF. Further, p1C11 also effectively inhibited VEGF-stimulated activation of MAP kinases p44/p42. In contrast, neither p1C11, nor p2A6 inhibited FGF-stimulated activation of MAP kinases p44/p42.

Example IX-2(d)
Anti-Mitogenic Assay

HUVEC (5×103 cells/well) were plated onto 96-well tissue culture plates (Wallach, Inc., Gaithersburg, Md.) in 200 μl of EBM-2 medium without VEGF, bFGF or EGF and incubated at 37° C. for 72 h. Various amounts of antibodies were added to duplicate wells and pre-incubated at 37° C. for 1 h, after which $VEGF_{165}$ was added to a final concentration of 16 ng/ml. After 18 h of incubation, 0.25 μCi of [3H]-TdR (Amersham) was added to each well and incubated for an additional 4 h. The cells were placed on ice, washed twice with serum-containing medium, followed by a 10 minute incubation at 4° C. with 10% TCA. The cells were then washed once with water and solubilized in 25 μl of 2% SDS. Scintillation fluid (150 μl/well) was added and DNA incorporated radioactivity was determined on a scintillation counter (Wallach, Model 1450 Microbeta Scintillation Counter).

Figure 18:
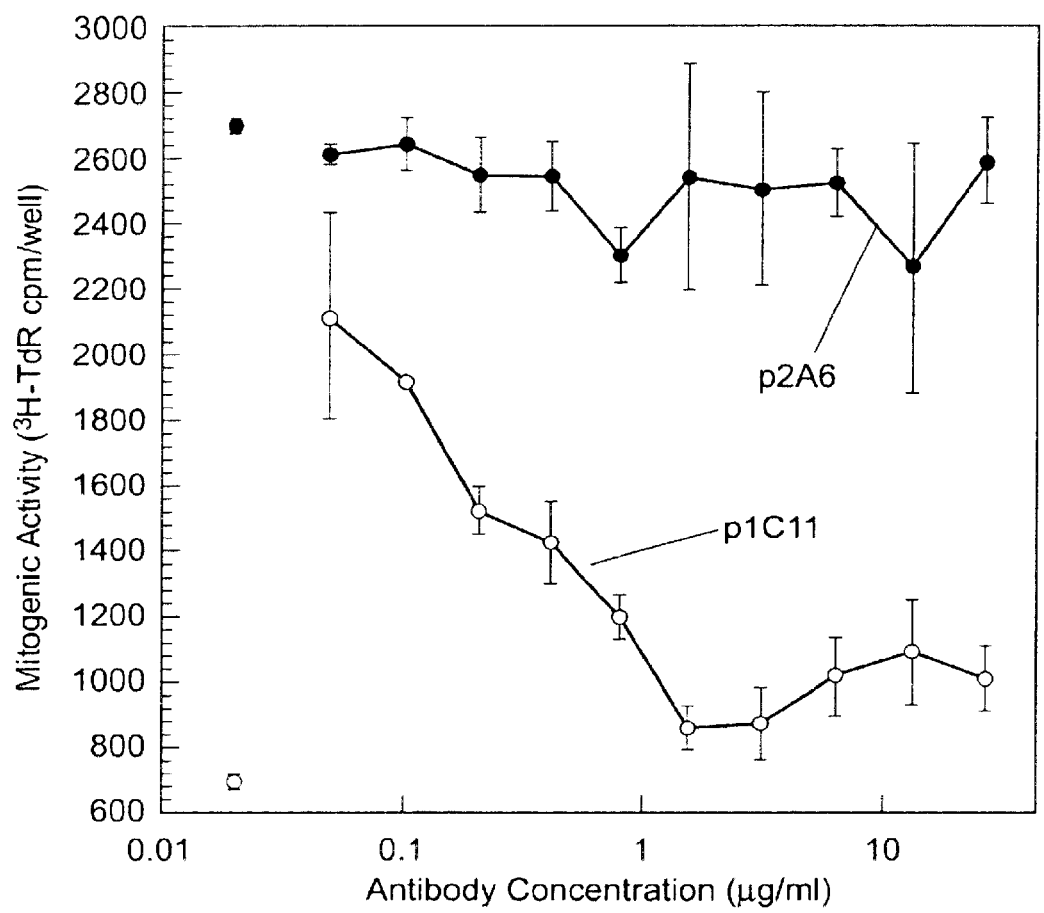
FIG. 18: A graph showing the inhibition of VEGF-induced HUVEC proliferation by scFv antibodies (p2A6 and p1C11).

The ability of scFv antibodies to block VEGF-stimulated mitogenic activity on HUVEC is shown in FIG. 18. The VEGF-blocking scFv p1C11strongly inhibited VEGF induced DNA synthesis in HUVEC with an $EC_{50}$, i.e., the antibody concentration that inhibited 50% of VEGF-stimulated mitogenesis of HUVEC, of approximately 5 nM. The non-blocking scFv p2A6 showed no inhibitory effect on the mitogenic activity of VEGF. Neither p1C11 nor p2A6 inhibited bFGF-induced DNA synthesis in HUVEC (not shown). Data shown in FIG. 18 are representative of at least three separate experiments. (■) VEGF only; (□) no VEGF.

Example IX-3
Producing Chimeric Antibodies from p1C11

Example IX-3(a)
Cell Lines and Proteins

Primary-cultured human umbilical vein endothelial cells (HUVEC) were maintained in EBM-2 medium at 37° C., 5% CO2. Cells between passage 2–5 were used for all assays. $VEGF_{165}$ and KDR-alkaline phosphatase fusion proteins (KDR-AP) were expressed in baculovirus and NIH 3T3 cells, respectively, and purfied following the procedures described above. The anti-KDR scFv p1C11 and scFv p2A6, an antibody that binds to KDR but does not block KDR-VEGF interaction, were isolated from a phage display library constructed from a mouse immunized with KDR as described above. C225 is a chimeric IgG1 antibody directed against epidermal growth factor (EGF) receptor. See above.

Example IX-3(b)
Cloning of the Variable Domains of scFv p1C11

The variable domains of the light ($V_L$) (SEQ ID NO: 8 and SEQ ID NO: 16) and the heavy ($V_H$) (SEQ ID NO: 7 and SEQ ID NO: 15) chains of p1C11 were cloned from the scFv expression vector by PCR using primers 1 and 2, and primers 3 and 4, respectively. The leader peptide sequence for protein secretion in mammalian cells was then added to the 5' of the $V_L$ and the $V_H$ by PCR using primers 5 and 2, and primers 5 and 4, respectively.

Primer 1: 5' CTA GTA GCA ACT GCA ACT GGA GTA CAT TCA GAC ATC GAG CTC3' [SEQ ID No: 37]
Primer 2: 5' TCG ATC TAG AA<u>G GAT CC</u>A CTC ACG TTT TAT TTC CAG3'BamHI [SEQ ID No: 38]
Primer 3: 5' CTA GTA GCA ACT GCA ACT GGA GTA CAT TCA CAG GTC AAG CTG3' [SEQ ID No: 39]
Primer 4: 5' TCG AA<u>G GAT CC</u>A CTC ACC TGA GGA GAC GGT3'BamHI [SEQ ID No: 40]
Primer 5: 5' GGT CAA <u>AAG CTT</u>ATG GGA TGG TCA TGT ATC ATC CTT TTT Hind III CTA GTA GCAACT3' [SEQ ID No: 41]

Example IX-3(c)
Construction of the Expression Vectors for the Chimeric p1C11 IgG Separate vectors for expression of chimeric IgG light chain and heavy chains were constructed. The cloned VL gene was digested with Hind III and BamH I and ligated into the vector pKN100 containing the human K light chain constant region ($C_L$) to create the expression vector for the chimeric p1C11 light chain, c-p1C11 -L. The cloned $V_H$ gene was digested with Hind III and BamH I and ligated into the vector pGID105 containing the human IgG1 (γ) heavy chain constant domain ($C_H$) to create the expression vector for the chimeric p1C11 heavy chain, c-p1C11-H. Both constructs were examined by restriction enzyme digestion and verified by dideoxynucleotide sequencing.

As seen in FIG. 19 both the $V_H$ and the $V_L$ domains are precisely fused on their 5' ends to a gene segment encoding a leader peptide sequence (SEQ ID NO: 23 and SEQ ID NO: 24) as marked. The $V_H$ and the $V_L$ domains are ligated via Hind III/BamH I sites into expression vector pG1D105, which contains a cDNA version of the human γl constant region gene, and pKN100, which contains a cDNA version of the human κ chain constant region gene, respectively. In each case, expression is under control of the HCMVi promoter and terminated by an artificial termination sequence. The light and the heavy chain complimentarily determining region (CDR) residues, defined according the hypervariable sequence definition of Kabat et al., are underlined and labeled CDR-H1 to H3 and CDR-L1 to L3, respectively. CDR-H1 (SEQ ID NO: 1 and SEQ ID NO: 9); CDR-H2 (SEQ ID NO: 2 and SEQ ID NO: 10); CDR-H3 (SEQ ID NO: 3 and SEQ ID NO: 11); CDR-L1 (SEQ ID NO: 4 and SEQ ID NO: 12); CDR-L2 (SEQ ID NO: 5 and SEQ ID NO: 13);. CDR-L3 (SEQ ID NO: 6 and SEQ ID NO: 14).

Example IX-3(d)
IgG Expression and Purification

COS cells were co-transfected with equal amounts of c-p1C11-L and c-p1C11-H plasmids for transient IgG expression. Subconfluent COS cells grown in DMEM/10% FCS in 150 mm culture dishes were rinsed once with 20 ml of DMEM containing 40 mM Tris (pH 7.4), followed by incubation at 37° C. for 4.5 h with 4 ml of DMEM/DEAE-Dextran/DNA mixture (DMEM containing 40 mM Tris, 0.4 mg/ml of DEAE-Dextran (Sigma), and 20 μg each of c-p1C11-L and c-p1C11-H plasmids). The cells were incubated at 37° C. for 1 h with 4 ml of DMEM/2% FCS containing 100 nM of chloroquine (Sigma), followed by incubation with 1.5 ml of 20% glycerol/PBS at room temperature for 1 min. The cells were washed twice with DMEM/5% FCS and incubated in 20 ml of the same medium at 37° C. overnight. The cell culture medium was changed to serum-free DMEM/HEPES after the cells were washed twice with plain DMEM. The cell culture supernatant was collected at 48 h and 120 h after the transfection. The chimeric IgG was purified from the pooled supernatant by affinity chromatography using Protein G column following the protocol described by the manufacturer (Pharmacia Biotech). The IgG-containing fractions were pooled, buffer exchanged into PBS and concentrated using Centricon 10 concentrators (Amicon Corp., Beverly, Mass.). The purity of the IgG was analyzed by SDS-PAGE. The concentration of purified antibody was determined by ELISA using goat anti-human y chain specific antibody as the capture agent and HRP-conjugated goat anti-human k chain antibody as the detection agent. Standard curve was calibrated using a clinical grade antibody, C225.

After affinity purification by Protein G, a single protein band of ~150 kD was seen in SDS-PAGE. Western blot analysis using HRP-conjugated anti-human IgG1 Fc specific antibody confirmed the presence of human IgG Fc portion in the purified protein (not shown).

Figure 20:
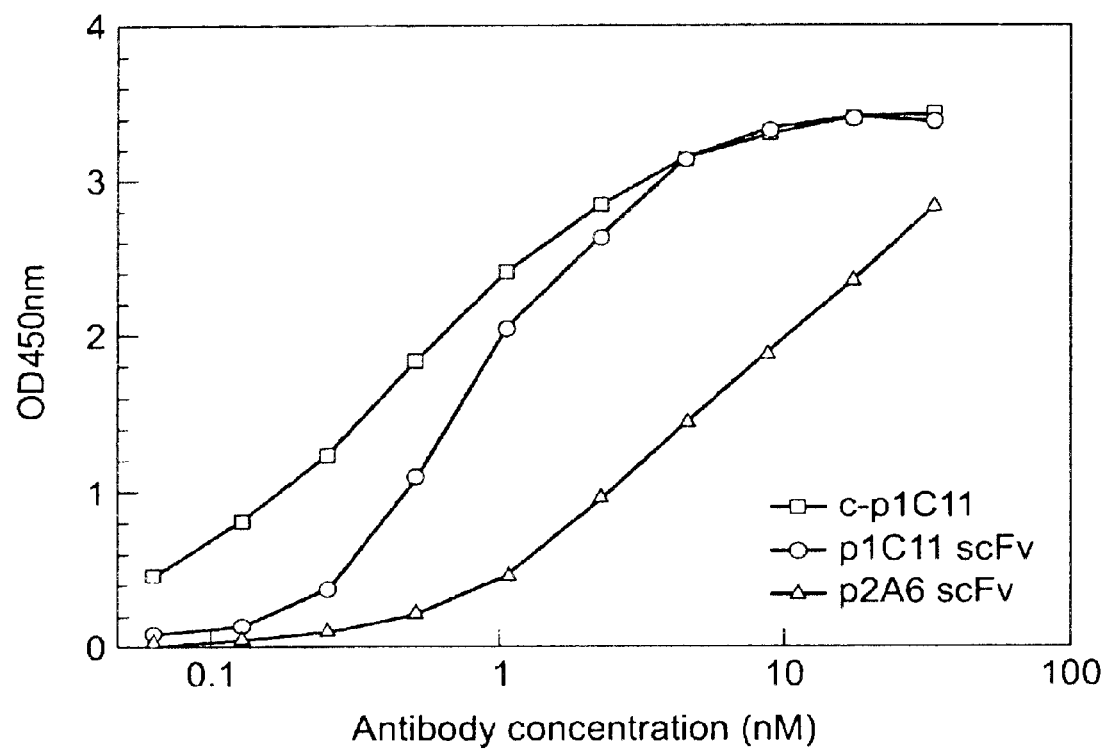
FIG. 20: A graph showing the direct binding of antibodies (c-p1C11, p1C11, p2A6) to immobilized KDR.

The results of the ELISA show that c-p1C11 binds more efficiently to immobilized KDR than the parent scFv (FIG. 20).

Example IX-4
Assays and Analysis

Example IX-4(a)
FACS Analysis

Early passage HUVEC cells were grown in growth factor-depleted EBM-2 medium overnight to induce the expression of KDR. The cells were harvested and washed three times with PBS, incubated with c-p1C11 IgG (5 μg/ml) for 1 h at 4° C., followed by incubation with a FITC labeled rabbit anti-human Fc antibody (Capper, Organon Teknika Corp., West Chester, Pa.) for an additional 60 min. The cells were washed and analyzed by a flow cytometer (Model EPICS®, Coulter Corp., Edison, N.J.).

Figure 21:
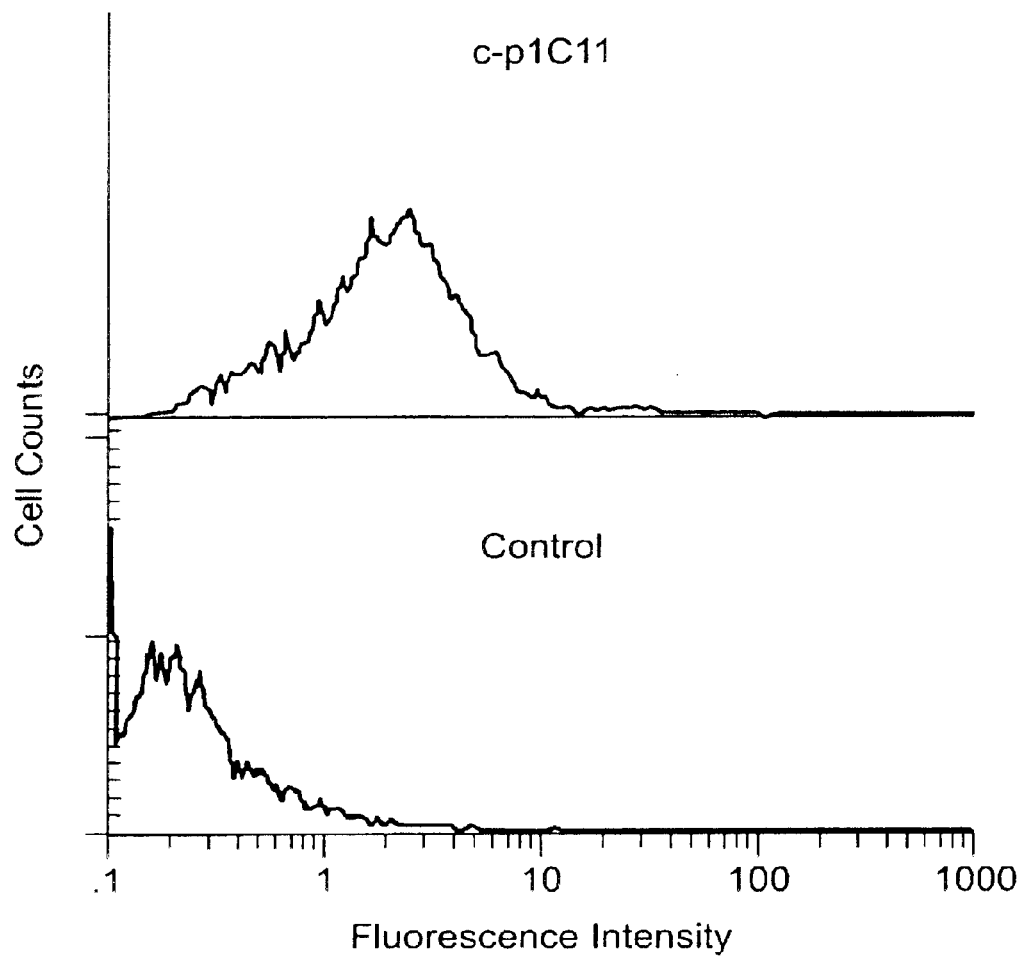
FIG. 21: A graph showing the FACS analysis of c-p1C11 binding to KDR-expressing HUVEC.

FIG. 21 is a graph showing the FACS analysis of c-p1C11 binding to KDR-expressing HUVEC. As previously seen with the parent scFv p1C11, c-p1C11 binds specifically to KDR expressed on early passage HUVEC.

Example IX-4(b)
Quantitative KDR Binding Assay

Various amounts of antibodies were added to KDR-coated 96-well Maxi-sorp microtiter plates (Nunc. Danmark) and incubated at room temperature for 1 h, after which the plates were washed 3 times with PBS containing 0.1% Tween-20. The plates were then incubated at RT for 1 h with 100 µl of mouse anti-E tag antibody-HRP conjugate (Phannacia Biotech) for the scFv, or rabbit anti-human IgG Fc specific antibody-HRP conjugate (Cappel, Organon Teknika Corp.) for the chimeric IgG. The plates were washed 5 times, TMB peroxidase substrate (KPL, Gaithersburg, Md.) added, and the OD at 450 nm read using a microplate reader (Molecular Device, Sunnyvale, Calif.).

FIG. 20 is a graph showing the direct binding of antibodies to immobilized KDR. C-p1C11 is shown to bind more efficiently to immobilized KDR receptor than the parent scFv.

Example IX-4(c)
BIA Core Analysis

The binding kinetics of antibodies to KDR were measured using BIAcore biosensor (Pharmacia Biosensor). KDR-AP fusion protein was immobilized onto a sensor chip, and antibodies or VEGF were injected at concentrations ranging from 25 nM to 200 nM. Sensorgrams were obtained at each concentration and were evaluated using a program, BIA Evaluation 2.0, to determine the rate constants kon and koff. Kd was calculated as the ratio of rate constants koff/kon.

BIAcore analysis reveals that c-p1C11 bind to KDR with higher affinity than the parent scFv (Table 2). The Kd of c-p1C11 is 0.82 nM, compared to 2.1 nM for the scFv. The increased affinity of c-p1C11 is mainly due to a slower dissociation rate (koff) of the bivalent chimeric IgG. It is important to note that the affinity (Kd) of c-p1C11 for binding to KDR is similar to that of the natural ligand VEGF for binding to KDR, which is 0.93 nM as determined in our BIAcore analysis (Table 2).

Example IX-4(d)
Competitive VEGF Binding Assay

In the first assay, various amounts of antibodies were mixed with a fixed amount of KDR-AP (50 ng) and incubated at room temperature for 1 h. The mixtures were then transferred to 96-well microtiter plates coated with $VEGF_{165}$ (200 ng/well) and incubated at room temperature for an additional 2 h, after which the plates were washed 5 times and the substrate for AP (p-nitrophenyl phosphate, Sigma) was added to quantify the bound KDR-AP molecules. $EC_{50}$, i.e., the antibody concentration required for 50% inhibition of KDR binding to VEGF, was then calculated.

Figure 22:
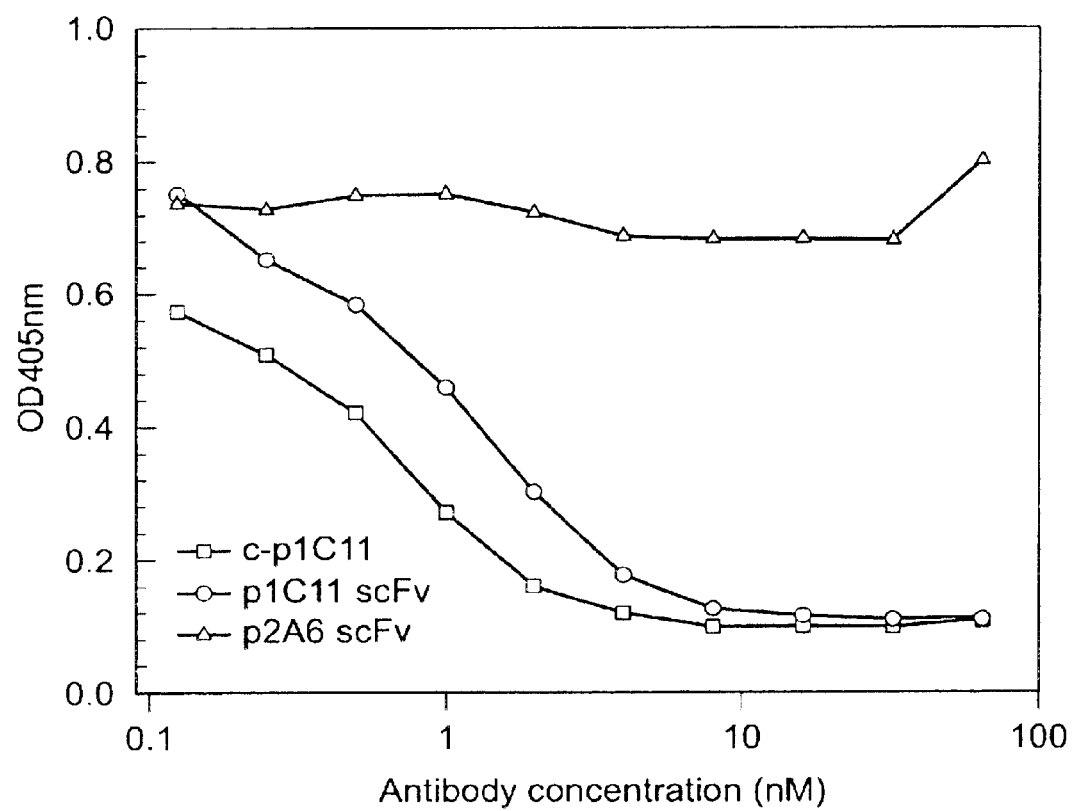
FIG. 22: A graph showing the inhibition of binding of KDR receptor to immobilized $VEGF_{165}$ by different scFv antibodies (c-p1C11, p1C11, p2A6).

FIG. 22 shows that c-p1C11 block KDR receptor from binding to immobilized VEGF in a dose-dependent manner. The chimeric antibody is more potent in blocking VEGF-KDR interaction with an $IC_{50}$ (i.e., the antibody concentrations required to inhibit 50% of KDR from binding to VEGF) of 0.8 nM, compared to that of 2.0 nM for the scFv. The control scFv p2A6 also binds KDR (FIG. 20) but does not block VEGF-KDR interaction (FIG. 22).

In the second assay, various amounts of c-p1C11 antibody or cold $VEGF_{165}$ protein were mixed with a fixed amount of 125I labeled $VEGF_{165}$ and added to 96-well microtiter plates coated with KDR receptor. The plates were incubated at room temperature for 2h, washed 5 times and the amounts of radiolabeled $VEGF_{165}$ that bound to immobilized KDR receptor were counted. Concentrations of c-p1C11 and cold $VEGF_{165}$ required to block 50% of binding of the radiolabeled VEGF to immobilized KDR receptor were determined.

Figure 23:
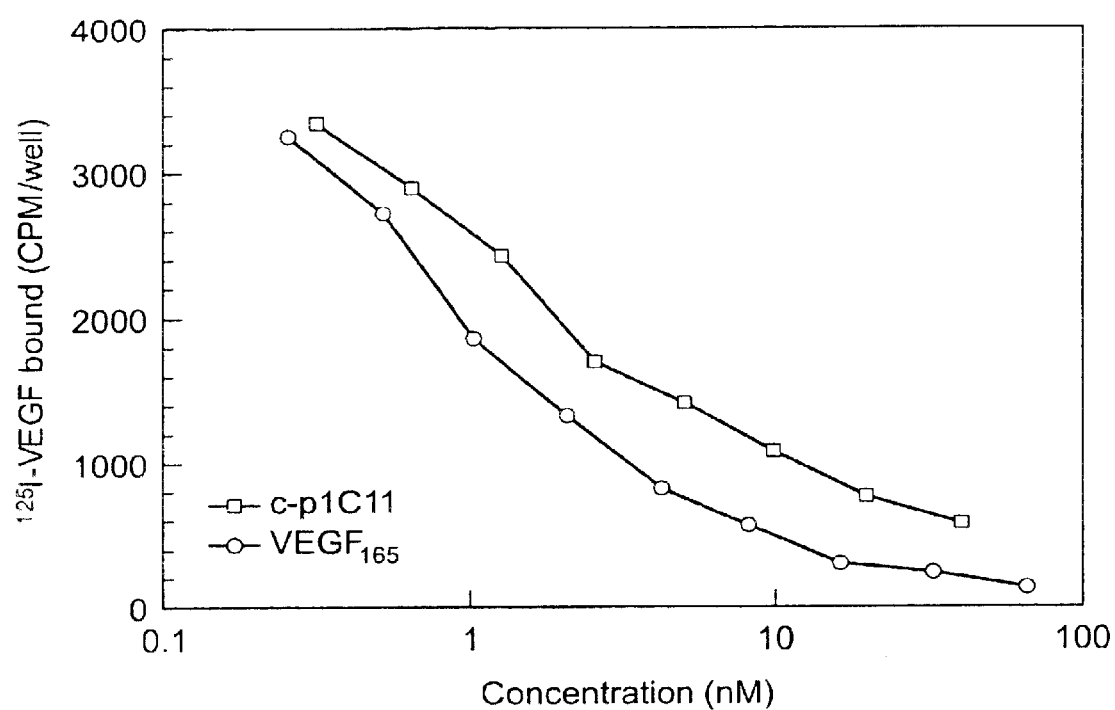
FIG. 23: A graph showing the inhibition of binding of radiolabeled $VEGF_{165}$ to immobilized KDR receptor by c-p1C11 and cold $VEGF_{165}$.

The results of the inhibition of binding of radiolabeled $VEGF_{65}$ is shown in FIG. 23. The data shown are the means of triplicate determinations. c-p1C11 is shown to efficiently compete with $^{125}I$ labeled VEGF for binding to immobilized KDR receptor in a dose-dependent manner. As expected, C225, a chimeric antibody directed against EGF receptor does not bind to KDR receptor or block VEGF-KDR interaction (not shown).

Example IX-4(e)

Phosphorylation Assay

Subconfluent HUVEC cells were grown in growth factor depleted EBM-2 medium for 24 to 48 h prior to experimentation. After pretreatment with 50 nM sodium orthovanadate for 30 min, the cells were incubated in the presence or absence of antibodies for 15 min, followed by stimulation with 20 ng/ml of $VEGF_{165}$, or 10 ng/ml of FGF at room temperature for an additional 15 min. The cells were then lysed in lysis buffer (50 nM Tris, 150 mM NaCl, 1% NP-40, 2 mM EDTA, 0.25% sodium deoxycholate, 1 mM PMSF, 1 µg/ml leupeptin, 1 µg/ml pepstatin, 10 µg/ml aprotinin, pH 7.5) and the cell lysate used for both the KDR and MAP kinase phosphorylation assays. The KDR receptor was immunoprecipitated from the cell lysates with Protein A Sepharose beads (Santa Cruz Biotechnology, Inc., Calif.) coupled to an anti-KDR antibody, Mab 4.13 (ImClone Systems). Proteins were resolved with SDS-PAGE and subjected to Western blot analysis. To detect KDR phosphorylation, blots were probed with an antiphosphotyrosine Mab, PY20 (ICN Biomedicals, Inc. Aurora, Ohio). For the MAP kinase activity assay, cell lysates were resolved with SDS-PAGE followed by Western blot analysis using a phospho-specific MAP kinase antibody (New England BioLabs, Beverly, Mass.). All signals were detected using ECL (Amersham, Arlington Heights, Ill.). In both assays, the blots were reprobed with a polyclonal anti-KDR antibody (ImClone Systems) to assure that equal amount of protein was loaded in each lane of SDS-PAGE gels.

C-p1C11 effectively inhibits VEGF-stimulated phosphorylation of KDR receptor and activation of p44/p42 MAP kineses. In contrast, C225 does not show any inhibition of VEGF-stimulated activation of KDR receptor and MAP kineses. Neither c-p1C11, nor C225 alone has any effects on the activity of KDR receptor and p44/p42 MAP kinases. As previously seen with the scFv p1C11, c-p1C11 does not inhibit FGF-stimulated activation of p44/p42 MAP kinases (not shown). Furthermore, neither scFv p2A6, nor the chimeric IgG form of p2A6 (c-p2A6), inhibits VEGF-stimulated activation of KDR receptor and MAP kineses (not shown).

Example IX-4(f)
Anti-Mitogenic Assay

The effect of anti-KDR antibodies on VEGF-stimulated mitogenesis of human endothelial cells was determined with a [3H]-TdR DNA incorporation assay using HUVEC. HUVEC ($5\times10^3$ cells/well) were plated into 96-well tissue culture plates in 200 µl of EBM-2 medium without VEGF, bFGF or EGF and incubated at 37° C. for 72 h. Various amounts of antibodies were added to duplicate wells and pre-incubated at 37° C. for 1 hour, after which $VEGF_{165}$ was added to a final concentration of 16 ng/ml. After 18 hours of incubation, 0.25 µCi of [$^3$H]-TdR was added to each well and incubated for an additional 4 hours. DNA incorporated radioactivity was determined with a scintillation counter.

Figure 24:
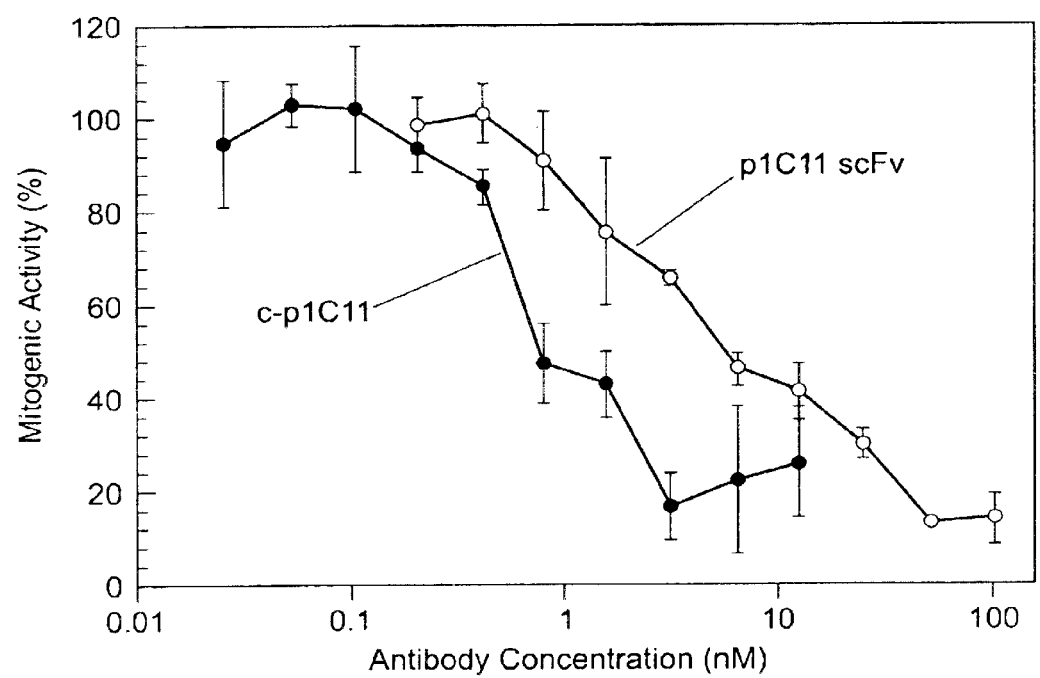
FIG. 24: A graph showing the inhibition of VEGF-induced HUVEC proliferation by anti-KDR antibodies (c-p1C11, p1C11).

The data shown in FIG. 24 are representative of at least three separate experiments.

Both c-p1C11 and scFv p1C11 effectively inhibit mitogenesis of HUVEC stimulated by VEGF (FIG. 24). C-p1C11 is a stronger inhibitor of VEGF-induced mitogenesis of HUVEC than the parent scFv. The antibody concentrations required to inhibit 50% of VEGF-induced mitogenesis of HUVEC are 0.8 nM for c-p1C11 and 6 nM for the scFv, respectively. As expected, scFv p2A6 does not show any inhibitory effect on VEGF-stimulated endothelial cell proliferation.

Supplemental Enablement

The invention as claimed is enabled in accordance with the above specification and readily available references and starting materials. Nevertheless, Applicants have deposited with the American Type Culture Collection, 12301 Parklawn Drive, Rockville, Md., 20852 U.S.A. (ATCC) the hybridoma cell lines that produce the monoclonal antibodies listed below:

Hybridoma cell line DC-101 producing rat anti-mouse FLK-1 monoclonal antibody deposited on Jan. 26, 1994 (ATCC Accession Number HB 11534).

Hybridoma cell line M25.18A1 producing mouse anti-mouse FLK-1 monoclonal antibody Mab 25 deposited on Jul. 19, 1996 (ATCC Accession Number HB 12152).

Hybridoma cell line M73.24 producing mouse anti-mouse FLK-1 monoclonal antibody Mab 73 deposited on Jul. 19, 1996 (ATCC Accession Number HB 12153).

These deposits were made under the provisions of the Budapest Treaty on the International Recognition of the Deposit of Microorganisms for the Purposes of Patent Procedure and the regulations thereunder (Budapest Treaty). This assures maintenance of a viable culture for 30 years from date of deposit. The organism will be made available by ATCC under the terms of the Budapest Treaty, and subject to an agreement between Applicants and ATCC which assures unrestricted availability upon issuance of the pertinent U.S. patent. Availability of the deposited strains is not to be construed as a license to practice the invention in contravention of the rights granted under the authority of any government in accordance with its patent laws.

TABLE 60

KDR - binding analysis of anti-KDR scFv antibodies

| ScFv clone | KDR binding[1] ($ED_{50}$, nM) | VEGF blocking[2] ($IC_{50}$, nM) | Binding kinetics[3] | | |
|---|---|---|---|---|---|
| | | | kon ($10^5$ $M^{-1}$ $s^{-1}$) | koff ($10^4$ $s^{-1}$) | Kd ($10^{-9}$ M) |
| P1C11 | Yes (0.3) | Yes (3.0) | 1.1 | 2.3 | 2.1 |
| P1F12 | Yes (1.0) | Yes (15) | 0.24 | 1.4 | 5.9 |
| P2A6 | Yes (5.0) | No (>300) | 4.1 | 46.1 | 11.2 |
| P2A7 | no (NA) | No (>300) | NA | NA | NA |

[1]Determined by direct binding ELISA, numbers in the parenthesis represent the scFv concentrations that give 50% of maximum binding;
[2]Determined by competitive VEGF blocking ELISA, numbers in the parenthesis represent the scFv concentrations required for 50% inhibition of KDR binding to immobilized VEGF;
[3]Determined by BIAcore analysis.
NA = not applicable.

TABLE 2

Binding kinetics of p1C11 scFv and c-p1C11 to KDR receptor.*

| Antibody | kon ($10^5$ $M^{-1}$ $s^{-1}$) | koff ($10^{-4}$ $s^{-1}$) | Kd ($10^{-9}$ M) |
|---|---|---|---|
| p1C11 scFv | 1.11 | 2.27 | 2.1 |
| c-p1C11 | 0.63 | 0.52 | 0.82 |
| VEGF | 1.87 | 1.81 | 0.93 |

*All rates are determined by surface plasmon resonance using BIAcore system, and are mean of at least three separate determinations.

What is claimed is:

1. A method for reducing tumor growth in a mammal in need thereof comprising treating the mammal with an effective amount of a combination of a monoclonal antibody which specifically binds to an extracellular domain of a VEGF receptor and radiation.

2. A method according to claim 1 wherein the mammal is a human.

3. A method according to claim 1 wherein the monoclonal antibody is administered before radiation.

4. A method according to claim 1 wherein the monoclonal antibody is administered during radiation.

5. A method according to claim 1 wherein the monoclonal antibody is admimstcrcd after radiation.

6. A method according to claim 1 wherein the monoclonal antibody is administered before and during radiation.

7. A method according to claim 1 wherein the monoclonal antibody is administered during and after radiation.

8. A method according to claim 1 wherein the monoclonal antibody is administered before and after radiation.

9. A method according to claim 1 wherein the monoclonal antibody is administered before, during, and after radiation.

10. A method according to claim 1 wherein the source of the radiation is external to the mammal.

11. A method according to claim 1 wherein the source of radiation is internal to the mammal.

12. A method according to claim 1 wherein the antibody is c-p1C11.

13. A method for reducing tumor growth in a mammal in need thereof comprising treating the mammal with an effective amount of a combination of a monoclonal antibody which specifically binds to an extracellular domain of a VEGF receptor and a chemotherapeutic agent.

14. A method according to claim 13 wherein the chemotherapeutic agent is not conjugated to the VEGF receptor monoclonal antibody.

15. A method according to claim 13 wherein the mammal is a human.

16. A method according to claim 13 wherein the monoclonal antibody is administered before treatment with the chemotherapeutic agent.

17. A method according to claim 13 wherein the monoclonal antibody is administered during treatment with the chemotherapeutic agent.

18. A method according to claim 13 wherein the monoclonal antibody is administered after treatment with the chemotherapeutic agent.

19. A method according to claim 13 wherein the monoclonal antibody is administered before and during treatment with the chemotherapeutic agent.

20. A method according to claim 13 wherein the monoclonal antibody is administered during and after treatment with the chemotherapeutic agent.

21. A method according to claim 13 wherein the monoclonal antibody is administered before and after treatment with the chemotherapeutic agent.

22. A method according to claim 13 wherein the monoclonal antibody is administered before, during, and after treatment with the chemotherapeutic agent.

23. A method according to claim 13 wherein the chemotherapeutic agent is selected from the group consisting of cisplatin, dicarbazine, dactinomycin, mechlorethamine, streptozocin, cyclophosphamide, carmustine, lomustine, doxorubicin, daunorubicin, procarbazine, mitomycin, cytarabine, etoposide, methotrexate, 5-fluorouracil, vinblastine, vincristine, bleomycin, paclitaxel, docetaxel, aldesleukin, asparaginase, busulfan, carboplatin, cladribine, dacarbazine, floxuridine, fludarabine, hydroxyurea, ifosfamide, interferon alpha, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil, taxol, an additional growth factor receptor antagonist and combinations thereof.

24. A method according to claim 13 wherein the chemotherapeutic agent is selected from the group consisting of cisplatin, doxorubicin, taxol and combinations thereof.

25. A method according to claim 13 wherein the antibody is c-p1C11.

26. A method according to claim 23 wherein the additional antagonist is a small molecule.

27. A method according to claim 13 further comprising treating the mammal with radiation.

* * * * *

UNITED STATES PATENT AND TRADEMARK OFFICE
CERTIFICATE OF CORRECTION

PATENT NO. : 6,811,779 B2
DATED : November 2, 2004
INVENTOR(S) : Rockwell et al.

It is certified that error appears in the above-identified patent and that said Letters Patent is hereby corrected as shown below:

<u>Column 53,</u>
Line 23, change "admimstcrcd" to -- administered --;

<u>Column 54,</u>
Line 33, change "vinbiastine" to -- vinblastine --.

Signed and Sealed this

Second Day of May, 2006

JON W. DUDAS
*Director of the United States Patent and Trademark Office*

SEQUENCE LISTING

<160> NUMBER OF SEQ ID NOS: 41

<210> SEQ ID NO 1
<211> LENGTH: 10
<212> TYPE: PRT
<213> ORGANISM: Mouse

<400> SEQUENCE: 1

Gly Phe Asn Ile Lys Asp Phe Tyr Met His
 1               5                  10

<210> SEQ ID NO 2
<211> LENGTH: 16
<212> TYPE: PRT
<213> ORGANISM: Mouse

<400> SEQUENCE: 2

Trp Ile Asp Pro Glu Asn Gly Asp Ser Asp Tyr Ala Pro Lys Phe Gln
 1               5                  10                  15

<210> SEQ ID NO 3
<211> LENGTH: 8
<212> TYPE: PRT
<213> ORGANISM: Mouse

<400> SEQUENCE: 3

Tyr Tyr Gly Asp Tyr Glu Gly Tyr
 1               5

<210> SEQ ID NO 4
<211> LENGTH: 10
<212> TYPE: PRT
<213> ORGANISM: Mouse

<400> SEQUENCE: 4

Ser Ala Ser Ser Ser Val Ser Tyr Met His
 1               5                  10

<210> SEQ ID NO 5
<211> LENGTH: 7
<212> TYPE: PRT
<213> ORGANISM: Mouse

<400> SEQUENCE: 5

Ser Thr Ser Asn Leu Ala Ser
 1               5

<210> SEQ ID NO 6
<211> LENGTH: 9
<212> TYPE: PRT
<213> ORGANISM: Mouse

<400> SEQUENCE: 6

Gln Gln Arg Ser Ser Tyr Pro Phe Thr
 1               5

<210> SEQ ID NO 7
<211> LENGTH: 117
<212> TYPE: PRT
<213> ORGANISM: Mouse

<400> SEQUENCE: 7

Gln Val Lys Leu Gln Gln Ser Gly Ala Glu Leu Val Gly Ser Gly Ala

```
            1               5              10              15
Ser Val Lys Leu Ser Cys Thr Thr Ser Gly Phe Asn Ile Lys Asp Phe
                20              25              30

Tyr Met His Trp Val Lys Gln Arg Pro Glu Gln Gly Leu Glu Trp Ile
        35              40              45

Gly Trp Ile Asp Pro Glu Asn Gly Asp Ser Asp Tyr Ala Pro Lys Phe
    50              55              60

Gln Gly Lys Ala Thr Met Thr Ala Asp Ser Ser Asn Thr Ala Tyr
65              70              75              80

Leu Gln Leu Ser Ser Leu Thr Ser Glu Asp Thr Ala Val Tyr Tyr Cys
                85              90              95

Asn Ala Tyr Tyr Gly Asp Tyr Glu Gly Tyr Trp Gly Gln Gly Thr Thr
            100             105             110

Val Thr Val Ser Ser
        115

<210> SEQ ID NO 8
<211> LENGTH: 106
<212> TYPE: PRT
<213> ORGANISM: Mouse

<400> SEQUENCE: 8

Asp Ile Glu Leu Thr Gln Ser Pro Ala Ile Met Ser Ala Ser Pro Gly
1               5              10              15

Glu Lys Val Thr Ile Thr Cys Ser Ala Ser Ser Val Ser Tyr Met
                20              25              30

His Trp Phe Gln Gln Lys Pro Gly Thr Ser Pro Lys Leu Trp Ile Tyr
            35              40              45

Ser Thr Ser Asn Leu Ala Ser Gly Val Pro Ala Arg Phe Ser Gly Ser
    50              55              60

Gly Ser Gly Thr Ser Tyr Ser Leu Thr Ile Ser Arg Met Glu Ala Glu
65              70              75              80

Asp Ala Ala Thr Tyr Tyr Cys Gln Gln Arg Ser Ser Tyr Pro Phe Thr
                85              90              95

Phe Gly Ser Gly Thr Lys Leu Glu Ile Lys
            100             105

<210> SEQ ID NO 9
<211> LENGTH: 30
<212> TYPE: DNA
<213> ORGANISM: Mouse

<400> SEQUENCE: 9
ggcttcaaca ttaaagactt ctatatgcac                                   30

<210> SEQ ID NO 10
<211> LENGTH: 51
<212> TYPE: DNA
<213> ORGANISM: Mouse

<400> SEQUENCE: 10
tggattgatc ctgagaatgg tgattctgat tatgccccga agttccaggg c            51

<210> SEQ ID NO 11
<211> LENGTH: 24
<212> TYPE: DNA
<213> ORGANISM: Mouse

<400> SEQUENCE: 11
```

-continued

| tactatggtg actacgaagg ctac | 24 |

<210> SEQ ID NO 12
<211> LENGTH: 30
<212> TYPE: DNA
<213> ORGANISM: Mouse

<400> SEQUENCE: 12

| agtgccagct caagtgtaag ttacatgcac | 30 |

<210> SEQ ID NO 13
<211> LENGTH: 21
<212> TYPE: DNA
<213> ORGANISM: Mouse

<400> SEQUENCE: 13

| agcacatcca acctggcttc t | 21 |

<210> SEQ ID NO 14
<211> LENGTH: 27
<212> TYPE: DNA
<213> ORGANISM: Mouse

<400> SEQUENCE: 14

| cagcaaagga gtagttaccc attcacg | 27 |

<210> SEQ ID NO 15
<211> LENGTH: 351
<212> TYPE: DNA
<213> ORGANISM: Mouse

<400> SEQUENCE: 15

| caggtcaagc tgcagcagtc tggggcagag cttgtggggt caggggcctc agtcaaattg | 60 |
| tcctgcacaa cttctggctt caacattaaa gacttctata tgcactgggt gaagcagagg | 120 |
| cctgaacagg gcctggagtg gattggatgg attgatcctg agaatggtga ttctgattat | 180 |
| gccccgaagt tccagggcaa ggccaccatg actgcagact catcctccaa cacagcctac | 240 |
| ctgcagctca gcagcctgac atctgaggac actgccgtct attactgtaa tgcatactat | 300 |
| ggtgactacg aaggctactg gggccaaggg accacggtca ccgtctcctc a | 351 |

<210> SEQ ID NO 16
<211> LENGTH: 318
<212> TYPE: DNA
<213> ORGANISM: Mouse

<400> SEQUENCE: 16

| gacatcgagc tcactcagtc tccagcaatc atgtctgcat ctccagggga gaaggtcacc | 60 |
| ataacctgca gtgccagctc aagtgtaagt tacatgcact ggttccagca gaagccaggc | 120 |
| acttctccca aactctggat ttatagcaca tccaacctgg cttctggagt ccctgctcgc | 180 |
| ttcagtggca gtggatctgg gacctcttac tctctcacaa tcagccgaat ggaggctgaa | 240 |
| gatgctgcca cttattactg ccagcaaagg agtagttacc cattcacgtt cggctcgggg | 300 |
| accaagctgg aaataaaa | 318 |

<210> SEQ ID NO 17
<211> LENGTH: 15
<212> TYPE: PRT
<213> ORGANISM: Mouse

-continued

```
<400> SEQUENCE: 17

Gly Gly Gly Gly Ser Gly Gly Gly Ser Gly Gly Gly Ser
1               5                   10                  15

<210> SEQ ID NO 18
<211> LENGTH: 45
<212> TYPE: DNA
<213> ORGANISM: Mouse

<400> SEQUENCE: 18
ggtggaggcg gttcaggcgg aggtggctct ggcggtggcg gatcg            45

<210> SEQ ID NO 19
<211> LENGTH: 10
<212> TYPE: PRT
<213> ORGANISM: Mouse

<400> SEQUENCE: 19

Gly Gly Gly Gly Ser Gly Gly Gly Gly Ser
1               5                   10

<210> SEQ ID NO 20
<211> LENGTH: 15
<212> TYPE: DNA
<213> ORGANISM: Mouse

<400> SEQUENCE: 20
ggtggaggcg gttca                                             15

<210> SEQ ID NO 21
<211> LENGTH: 238
<212> TYPE: PRT
<213> ORGANISM: Mouse

<400> SEQUENCE: 21

Gln Val Lys Leu Gln Gln Ser Gly Ala Glu Leu Val Gly Ser Gly Ala
1               5                   10                  15

Ser Val Lys Leu Ser Cys Thr Thr Ser Gly Phe Asn Ile Lys Asp Phe
                20                  25                  30

Tyr Met His Trp Val Lys Gln Arg Pro Glu Gln Gly Leu Glu Trp Ile
            35                  40                  45

Gly Trp Ile Asp Pro Glu Asn Gly Asp Ser Asp Tyr Ala Pro Lys Phe
        50                  55                  60

Gln Gly Lys Ala Thr Met Thr Ala Asp Ser Ser Ser Asn Thr Ala Tyr
    65                  70                  75                  80

Leu Gln Leu Ser Ser Leu Thr Ser Glu Asp Thr Ala Val Tyr Tyr Cys
                85                  90                  95

Asn Ala Tyr Tyr Gly Asp Tyr Glu Gly Tyr Trp Gly Gln Gly Thr Thr
            100                 105                 110

Val Thr Val Ser Ser Gly Gly Gly Gly Ser Gly Gly Gly Gly Ser Gly
        115                 120                 125

Gly Gly Gly Ser Asp Ile Glu Leu Thr Gln Ser Pro Ala Ile Met Ser
    130                 135                 140

Ala Ser Pro Gly Glu Lys Val Thr Ile Thr Cys Ser Ala Ser Ser Ser
145                 150                 155                 160

Val Ser Tyr Met His Trp Phe Gln Gln Lys Pro Gly Thr Ser Pro Lys
                165                 170                 175

Leu Trp Ile Tyr Ser Thr Ser Asn Leu Ala Ser Gly Val Pro Ala Arg
            180                 185                 190
```

Phe Ser Gly Ser Gly Ser Gly Thr Ser Tyr Ser Leu Thr Ile Ser Arg
            195                 200                 205

Met Glu Ala Glu Asp Ala Ala Thr Tyr Tyr Cys Gln Gln Arg Ser Ser
    210                 215                 220

Tyr Pro Phe Thr Phe Gly Ser Gly Thr Lys Leu Glu Ile Lys
225                 230                 235

<210> SEQ ID NO 22
<211> LENGTH: 714
<212> TYPE: DNA
<213> ORGANISM: Mouse

<400> SEQUENCE: 22

```
caggtcaagc tgcagcagtc tggggcagag cttgtggggt caggggcctc agtcaaattg        60
tcctgcacaa cttctggctt caacattaaa gacttctata tgcactgggt gaagcagagg       120
cctgaacagg gcctgagtg gattggatgg attgatcctg agaatggtga ttctgattat       180
gccccgaagt tccagggcaa ggccaccatg actgcagact catcctccaa cacagcctac       240
ctgcagctca gcagcctgac atctgaggac actgccgtct attactgtaa tgcatactat       300
ggtgactacg aaggctactg gggccaaggg accacggtca ccgtctcctc aggtggaggc       360
ggttcaggcg gaggtggctc tggcggtggc ggatcggaca tcgagctcac tcagtctcca       420
gcaatcatgt ctgcatctcc aggggagaag gtcaccataa cctgcagtgc cagctcaagt       480
gtaagttaca tgcactggtt ccagcagaag ccaggcactt ctcccaaact ctggatttat       540
agcacatcca acctggcttc tggagtccct gctcgcttca gtggcagtgg atctgggacc       600
tcttactctc tcacaatcag ccgaatggag gctgaagatg ctgccactta ttactgccag       660
caaaggagta gttacccatt cacgttcggc tcggggacca agctggaaat aaaa            714
```

<210> SEQ ID NO 23
<211> LENGTH: 19
<212> TYPE: PRT
<213> ORGANISM: Mouse

<400> SEQUENCE: 23

Met Gly Trp Ser Cys Ile Ile Leu Phe Leu Val Ala Thr Ala Thr Gly
1               5                   10                  15

Val His Ser

<210> SEQ ID NO 24
<211> LENGTH: 57
<212> TYPE: DNA
<213> ORGANISM: Mouse

<400> SEQUENCE: 24

```
atgggatggt catgtatcat cctttttcta gtagcaactg caactggagt acattca          57
```

<210> SEQ ID NO 25
<211> LENGTH: 15
<212> TYPE: DNA
<213> ORGANISM: Mouse

<400> SEQUENCE: 25

```
aactatggtg tacac                                                         15
```

<210> SEQ ID NO 26
<211> LENGTH: 5
<212> TYPE: PRT

```
<213> ORGANISM: Mouse

<400> SEQUENCE: 26

Asn Tyr Gly Val His
  1               5

<210> SEQ ID NO 27
<211> LENGTH: 48
<212> TYPE: DNA
<213> ORGANISM: Mouse

<400> SEQUENCE: 27
gtgatatgga gtggtggaaa cacagactat aatacacctt tcacatcc        48

<210> SEQ ID NO 28
<211> LENGTH: 16
<212> TYPE: PRT
<213> ORGANISM: Mouse

<400> SEQUENCE: 28

Val Ile Trp Ser Gly Gly Asn Thr Asp Tyr Asn Thr Pro Phe Thr Ser
  1               5                  10                  15

<210> SEQ ID NO 29
<211> LENGTH: 33
<212> TYPE: DNA
<213> ORGANISM: Mouse

<400> SEQUENCE: 29
gccctcacct actatgatta cgagtttgct tac                        33

<210> SEQ ID NO 30
<211> LENGTH: 11
<212> TYPE: PRT
<213> ORGANISM: Mouse

<400> SEQUENCE: 30

Ala Leu Thr Tyr Tyr Asp Tyr Glu Phe Ala Tyr
  1               5                  10

<210> SEQ ID NO 31
<211> LENGTH: 33
<212> TYPE: DNA
<213> ORGANISM: Mouse

<400> SEQUENCE: 31
agggccagtc agagtattgg cacaaacata cac                        33

<210> SEQ ID NO 32
<211> LENGTH: 11
<212> TYPE: PRT
<213> ORGANISM: Mouse

<400> SEQUENCE: 32

Arg Ala Ser Gln Ser Ile Gly Thr Asn Ile His
  1               5                  10

<210> SEQ ID NO 33
<211> LENGTH: 18
<212> TYPE: DNA
<213> ORGANISM: Mouse

<400> SEQUENCE: 33
gcttctgagt ctatctct                                         18
```

<210> SEQ ID NO 34
<211> LENGTH: 6
<212> TYPE: PRT
<213> ORGANISM: Mouse

<400> SEQUENCE: 34

Ala Ser Glu Ser Ile Ser
 1               5

<210> SEQ ID NO 35
<211> LENGTH: 27
<212> TYPE: DNA
<213> ORGANISM: Mouse

<400> SEQUENCE: 35
caacaaaata ataactggcc aaccacg                                      27

<210> SEQ ID NO 36
<211> LENGTH: 9
<212> TYPE: PRT
<213> ORGANISM: Mouse

<400> SEQUENCE: 36

Gln Gln Asn Asn Asn Trp Pro Thr Thr
 1               5

<210> SEQ ID NO 37
<211> LENGTH: 42
<212> TYPE: DNA
<213> ORGANISM: Mouse

<400> SEQUENCE: 37
ctagtagcaa ctgcaactgg agtacattca gacatcgagc tc                    42

<210> SEQ ID NO 38
<211> LENGTH: 36
<212> TYPE: DNA
<213> ORGANISM: Mouse

<400> SEQUENCE: 38
tcgatctaga aggatccact cacgttttat ttccag                           36

<210> SEQ ID NO 39
<211> LENGTH: 42
<212> TYPE: DNA
<213> ORGANISM: Mouse

<400> SEQUENCE: 39
ctagtagcaa ctgcaactgg agtacattca caggtcaagc tg                    42

<210> SEQ ID NO 40
<211> LENGTH: 30
<212> TYPE: DNA
<213> ORGANISM: Mouse

<400> SEQUENCE: 40
tcgaaggatc cactcacctg aggagacggt                                  30

<210> SEQ ID NO 41
<211> LENGTH: 51
<212> TYPE: DNA
<213> ORGANISM: Mouse

```
-continued

<400> SEQUENCE: 41
ggtcaaaagc ttatgggatg gtcatgtatc atccttttttc tagtagcaac t                51
```